United States Patent [19]

Uemura et al.

[11] Patent Number: 5,197,105
[45] Date of Patent: Mar. 23, 1993

[54] METHOD OF READING OPTICAL IMAGE OF INSPECTED SURFACE AND IMAGE READING SYSTEM EMPLOYABALE THEREIN

[75] Inventors: Haruo Uemura; Tetsuo Hoki, both of Kyoto, Japan

[73] Assignee: Dainippon Screen Mfg. Co. Ltd., Japan

[21] Appl. No.: 706,801

[22] Filed: May 29, 1991

[30] Foreign Application Priority Data

May 30, 1990 [JP] Japan .................... 2-142889
May 30, 1990 [JP] Japan .................... 2-142890
Apr. 11, 1991 [JP] Japan .................... 3-033354

[51] Int. Cl.$^5$ ............................... G06K 9/00
[52] U.S. Cl. ....................... 382/8; 356/237; 356/435; 358/106; 382/62; 382/65
[58] Field of Search ............ 382/8, 65, 58, 62, 66–68; 358/101, 106, 107; 356/435, 382, 384, 386, 237

[56] References Cited

U.S. PATENT DOCUMENTS

| | | | |
|---|---|---|---|
| 4,635,289 | 1/1987 | Doyle et al. | 382/8 |
| 4,744,047 | 5/1988 | Okamoto et al. | 382/8 |
| 4,794,647 | 12/1988 | Forgues et al. | 382/8 |
| 4,845,558 | 7/1989 | Tsui et al. | 358/106 |
| 4,893,346 | 1/1990 | Bishop | 382/8 |
| 4,922,308 | 5/1990 | Noguchi et al. | 382/8 |
| 5,027,295 | 6/1991 | Yotsoya | 358/106 |

OTHER PUBLICATIONS

"Optical Device for Inspecting Appearance of Pattern of Printed Circuit Board", Electronic Packaging Technology, vol. 8, No. 3, pp. 42–45, 1985-Japan.
"Structure and the Present Situation of Automation System of Visual Inspection", Pixel, No. 42, pp. 70–72, 1986, published by Figure Processing Information Center, Japan.

Primary Examiner—Joseph Mancuso
Attorney, Agent, or Firm—Ostrolenk, Faber, Gerb & Soffen

[57] ABSTRACT

A set of red light sources (111–113) are provided above a printed board (20). One (111) of the light sources located in the angular aperture of an imaging lens system (140). The red light is applied to the printed board and reflected on a wiring pattern (22) provided thereon. Another light source (120) is provided under the printed board, and emits infrared light to the back surface of the printed board. The infrared light passes through a through hole (25) formed in the printed board and then enters the imaging lens system together with the red light reflected. Compound light consisting of the red light and the infrared light passes through the imaging lens system and is then splitted into the red light and the infrared light at a cold mirror (150). The respective lights are detected by image sensors (161, 162), to thereby obtain respective images of the wiring pattern and the through hole.

47 Claims, 34 Drawing Sheets

D = 0.3mm
H = 1.6mm

F I G. 10A
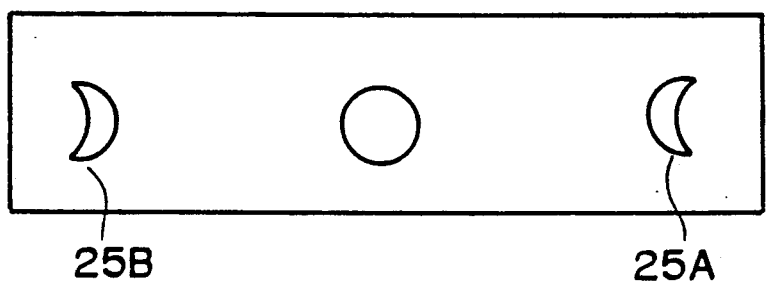
F I G. 10B
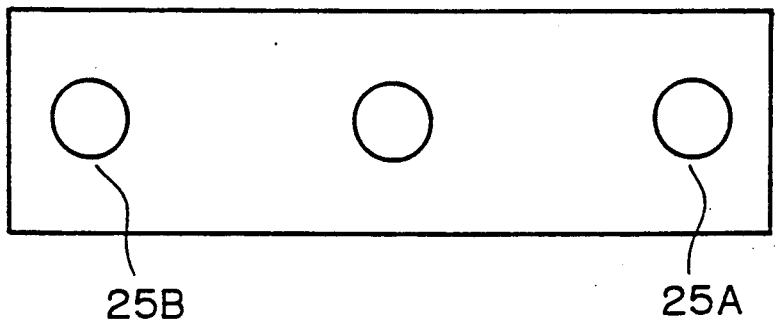

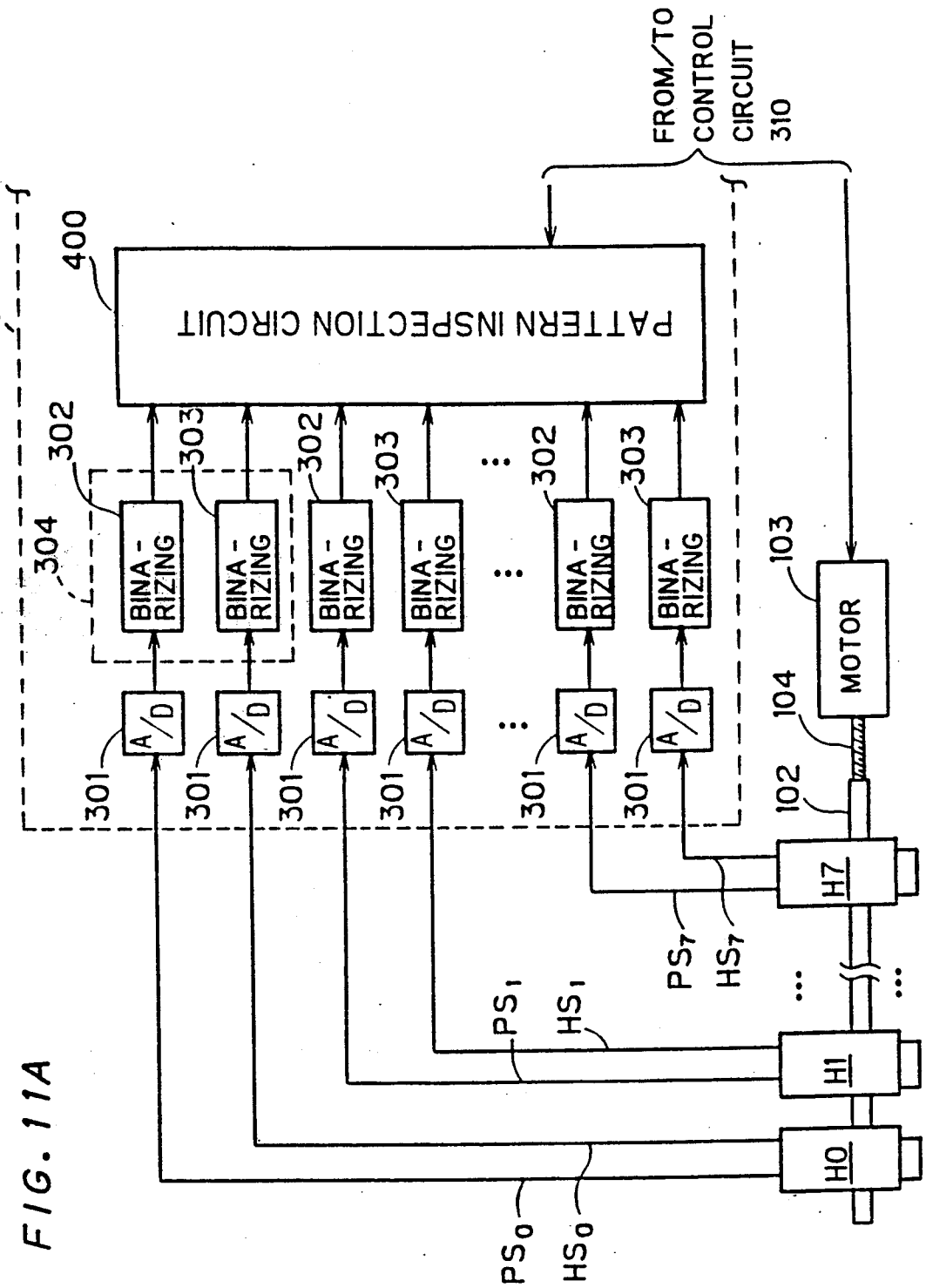

METHOD OF READING OPTICAL IMAGE OF INSPECTED SURFACE AND IMAGE READING SYSTEM EMPLOYABALE THEREIN

BACKGROUND OF THE INVENTION

1. Field of the Invention

The present invention relates to a method of reading the optical image of an inspected surface and an image reading system employable in an optical appearance inspecting apparatus for a printed circuit board etc. More particularly, the present invention relates to improvement for increasing incident light intensity in an image sensor equipped in the image reading system.

2. Description of the Background Art

As is well known in the art, a printed circuit board is provided with a metal wiring pattern on its one or each surface, while a through hole for accepting the lead wires of an electronic component is formed in a direction penetrating the circuit board. In order to inspect whether or not the wiring pattern and the through hole are formed with an accuracy within a predetermined tolerance, various types of optical appearance inspecting apparatuses are employed.

FIG. 27 is a conceptual diagram showing a conventional image reading system employed in a wiring pattern inspecting apparatus. Light 2 emitted from a light source 1 is reflected by a half mirror 3, and applied to the surface of a printed circuit board 5. The printed circuit board 5 is provided with a wiring pattern 6 and a through hole 7, and reflected light 8 obtained by reflection of the light 2 on the surface thereof is imaged on a linear image sensor 9 through the half mirror 3 and an imaging lens 4.

FIG. 28 shows exemplary incident photo-levels in the linear image sensor 9, which photo-levels correspond to a linear image along the line K—K in FIG. 27. The wiring pattern 6 has a large light reflectance since it is made of a metal, and an incident photo-level corresponding to the wiring pattern 6 is also large. On the other hand, an incident photo-level from an insulating base 5a of the circuit board 5 is relatively small, while the light 2 is transmitted through the through hole 7 downwardly from the circuit board 5 and the photo-level therefrom is substantially zero. Thus, it is possible to obtain the image of the wiring pattern 6 by discriminating the respective incident photo-levels using a threshold value TH.

The conventional apparatus shown in FIG. 27 is based on the premise that differences between the photo-levels from the respective regions 5a, 6 and 7 are large. However, the light reflectance on the surface of the wiring pattern 6 is not necessarily uniform, and the photo-level therefrom may fluctuate. Further, the waveforms of the photo-levels are complicated by reflected light from an inner wall portion of the through hole 7, so that the boundary between respective images of the wiring pattern 6 and the through hole 7 is confused.

In order to cope with such circumstances, there has been proposed such a system that another light source is provided on a back surface side of a printed circuit board and the image sensor detects not only the reflected light but also the light which is transmitted through a through hole from the light source newly provided. For example, Japanese Patent Publication Gazette No. 62-29737 (1987) discloses such a technique. Further, Japanese Patent Laying-Open Gazette No. 62-276443 (1987) discloses an apparatus for catching only a hole image.

However, these prior art methods have the following disadvantages (1) and (2).

(1) In the apparatus shown in FIG. 27, only half the intensity of the light 2 from the light source 1 is reflected by the half mirror 3 and directed to the printed circuit board 5. Further, only half the light 8 reflected by the printed circuit board 5 transmits through the half mirror 3 to reach the image sensor 9. Even if the light reflectance at the wiring pattern 6 is 100%, therefore, the intensity of light reaching the image sensor 9 is ¼ of that of the light that leaves the light source 1.

Thus, the intensity of the light received in the image sensor 9 is relatively small, and image detection accuracy is not necessarily high. This is a common problem not only in an apparatus employed for appearance inspection of a printed circuit board, but also in appearance inspecting apparatuses as to various inspected objects.

(2) In optical appearance inspection, it is necessary to independently grasp respective states of formation of the wiring pattern and the through hole, while interpositional relations between the wiring pattern and the through hole must also be inspected. Thus, there is required an inspecting apparatus, which can simultaneously catch respective images of the wiring pattern and the through hole. However, the aforementioned prior art methods are merely adapted to catch the image of only one of the wiring pattern image and the through hole image, and is not structured to simultaneously grasp both images. Therefore, when such a prior art approach is employed, it is necessary to separately detect the respective images in order to recognize interrelation between the position of the wiring pattern and that of the through hole and then calculate the positional relation between the two images. Therefore, the inspection time is increased and the system structure is complicated.

Such circumstances are particularly aggravated in the system in which the diameter of through holes provided in printed circuit boards is so gradually reduced that through holes (mini via holes) of 0.5 to 0.1 mm in diameter, for example, are employed.

SUMMARY OF THE INVENTION

The present invention is directed to an image reading system for reading an image of an object.

According to the present invention, the image reading system comprises: (a) imaging optical system facing the object; (b) light source means provided in a part of an angular aperture of the imaging optical system for emitting illumination light toward the object, wherein the illumination light is reflected on the object to become a reflected light; and (c) image sensor means provided in the opposite side of the object across the imaging optical system, for receiving the reflected light through the imaging optical system to obtain an image of the object.

Light from the light source means for reflective illumination is not applied to the object through any half mirror etc. While a part of the light reflected by the object is eclipsed by the light source means, the remaining part reaches the image sensor through the imaging optical system. Therefore, a considerable part of the light from the light source means is incident upon the image sensor, whereby image detection accuracy in the image sensor is improved. When the light source means is so arranged as to be in contact with the optical axis of the imaging optical system, the reflected light reaching the image sensor without being eclipsed by the light source means is about ½ of the reflected light progressing toward an entrance pupil of the image detection part.

In an aspect of the present invention, obtained is an image reading system employable for reading respective images of a wiring pattern and a through hole of an printed board having first and second surfaces opposite to each other. The wiring pattern is formed on the first surface and the through hole is provided between the first and second surfaces.

According to this aspect of the present invention, the image reading system comprises: (a) imaging optical system facing the first surface of the printed board; (b) first light source means facing the first surface of the printed board to emit a first light having a first wavelength to the first surface of the printed board, wherein the first light is reflected on the wiring pattern to become a reflected light; (c) second light source means facing the second surface of the printed board to emit a second light having a second wavelength to the second surface of the printed board, wherein the second light is transmitted through the through hole to become a transmitted light which is overlapped with the reflected light to obtain a compound light entering the imaging optical system; (d) light splitter means for receiving the compound light having passed through the imaging optical system to split the compound light into the reflected light and the transmitted light; (e) first image sensor means for receiving the reflected light to obtain an image of the wiring pattern; and (f) second image sensor means for receiving the transmitted light to obtain an image of the through hole.

The first light source means is adapted for reflective illumination of the wiring pattern, and the second light source means is adapted for transmitting illumination of the through hole.

The first light from the first light source means and the second light that from the second light source means are applied to a common area on the printed board, whereby reflected light from the wiring pattern and transmitted light from the through hole from the first spatially overlapped compound light. When the first light were identical in property to the second, therefore, it would be impossible to interseparate the reflected light and the transmitted light from each other.

According to the structure of the present invention, therefore, the first light for reflective illumination is different in wavelength from the second light for transmitting illumination. Thus, it is possible to interseparate the reflected wave and the transmitted wave from each other using a wavelength separation mirror etc. as light splitter means, whereby the wiring pattern and the through hole can be simultaneously and correctly detected.

Two types of light having different polarization directions may be employed in place of the two types of light having different wavelengths.

In this case, the reflected light and the transmitted light obtained from the first light and the second light can be separated using a polarized beam splitter, for example.

Preferably, a telecentric lens system, which is telecentric at least on the object side, is employed as the imaging optical system. Even if the through hole has a small diameter as a mini via hole, it is possible to correctly obtain an image using transmitted light therethrough.

In another aspect of the present invention, the image reading system comprises: (a) imaging optical system; and (b) a selective reflection mirror covering whole of an angular aperture of the imaging optical system.

The selective reflection mirror comprises a surface which consists of: a first region capable of reflecting a first light of a first optical character and capable of transmitting a second light of a second optical character; and a second region capable of reflecting the first and second lights. The angular aperture of the imaging optical system is divided into two part with a boundary of the first and second regions.

The image reading system further comprises: (c) first light source means provided out of an angular aperture of the imaging optical system, for emitting the first light toward the selective reflection mirror to direct the first light to the first surface of the printed board to obtain a reflected light through reflection of the first light on the wiring pattern; (d) second light source means provided in the second surface side, for emitting the second light toward the second surface of the printed board to obtain a transmitted light through transmittance of the second light through the through hole.

The reflected light and the transmitted light are overlapped with each other to form a compound light. The compound light enters the selective reflection mirror and then passes through the imaging optical system.

Also provided in the image reading system are; (e) light splitter means for receiving the compound light having passed through the imaging optical system to split the compound light into the reflected light and the transmitted light; (f) first image sensor means for receiving the reflected light to obtain an image of the wiring pattern; and (g) second image sensor means for receiving the transmitted light to obtain an image of the through hole.

In further another aspect of the present invention, the image reading system comprises: (a) imaging optical system; (b) a selective reflection mirror covering a part of an angular aperture of the imaging optical system and capable of reflecting a first light of a first optical character and capable of transmitting a second light of a second optical character; (c) first light source means provided out of an angular aperture of the imaging optical system, for emitting the first light toward the selective reflection mirror to direct the first light to the first surface of the printed board and to obtain a reflected light through reflection of the first light on the wiring pattern; and (d) second light source means provided in the second surface side, for emitting the second light toward the second surface of the printed board to obtain a transmitted light through transmittance of the second light through the through hole.

The reflected light and the transmitted light are overlapped with each other to form a compound light. The compound light passes through a space in which the selective reflection mirror is provided and then enters the imaging optical system.

With respect to the reflected light included in the compound light, only a part thereof bypassing the selective reflection mirror is received by the selective reflection mirror.

On the other hand, with respect to the transmitted light included in the compound light, both of a first part thereof passing through the selective reflection mirror and a second part bypassing the selective reflection mirror are received by the selective reflection mirror.

Also provided in the image reading system are: (e) light splitter means for receiving the compound light having passed through the imaging optical system to split the compound light into the reflected light and the transmitted light; (f) first image sensor means for receiving the reflected light with to obtain an image of the wiring pattern; and (g) second image sensor means for receiving the transmitted light to obtain an image of the through hole.

The wiring pattern is detected using reflective illumination with the first light source means and the through hole is detected using transmitting illumination with the second light source means. Therefore, illuminations suitable for respective object images are effectuated in parallel, and two lights obtained through respective illuminations are separated from each other.

The optical-amount of the light for transmitting illumination is fully usable in detection of the through hole image, and relatively large part of the light for regular reflection is usable in detection of the wiring pattern image.

Anisotropy in image detection signal of through hole is not caused unlike to the case where the light source for reflective illumination is arranged in the angular aperture of the imaging lens system.

As a result, detection of the respective images can be attained at a high speed and appearance inspection of printed circuit boards can be conducted at a high speed and in high accuracy.

The present invention is applicable not only to appearance inspection of a printed circuit board, but also to image reading systems in various inspecting apparatuses such as that for appearance inspection of a magnetic disk or a semiconductor wafer.

Accordingly, an object of the present invention is to provide an image reading system which increases the intensity of light received in an image sensor.

Another object of the present invention is to provide an image reading system which can simultaneously and correctly detect respective images of a wiring pattern and a through hole in a printed circuit board.

Further another object of the present invention is to perform appearance inspection at a high speed in high accuracy.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 10A and 10B illustrate hole images obtained through a non-telecentric lens system and a telecentric lens system, respectively;

FIGS. 11A, 11B and 11C illustrate an electrical structure of the apparatus shown in FIGS. 1A and 1B;

DESCRIPTION OF THE PREFERRED EMBODIMENTS

A. First Preferred Embodiment

A-1. Overall Structure

Figure 1A:
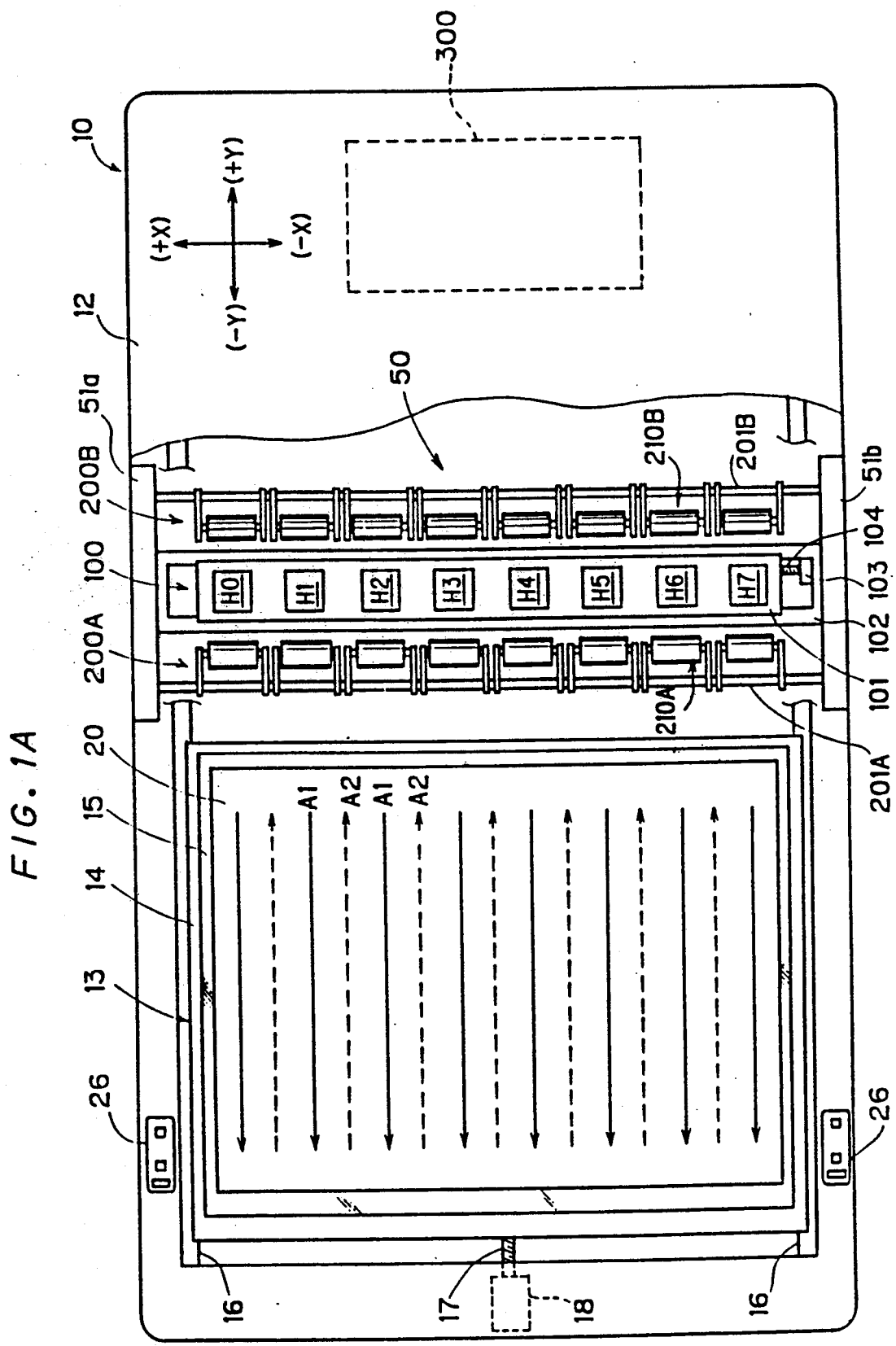
FIG. 1A is a partially fragmented plan view showing an optical inspecting apparatus for a printed circuit board in which an image reading system according to a preferred embodiment of the present invention is provided.
Figure 1B:
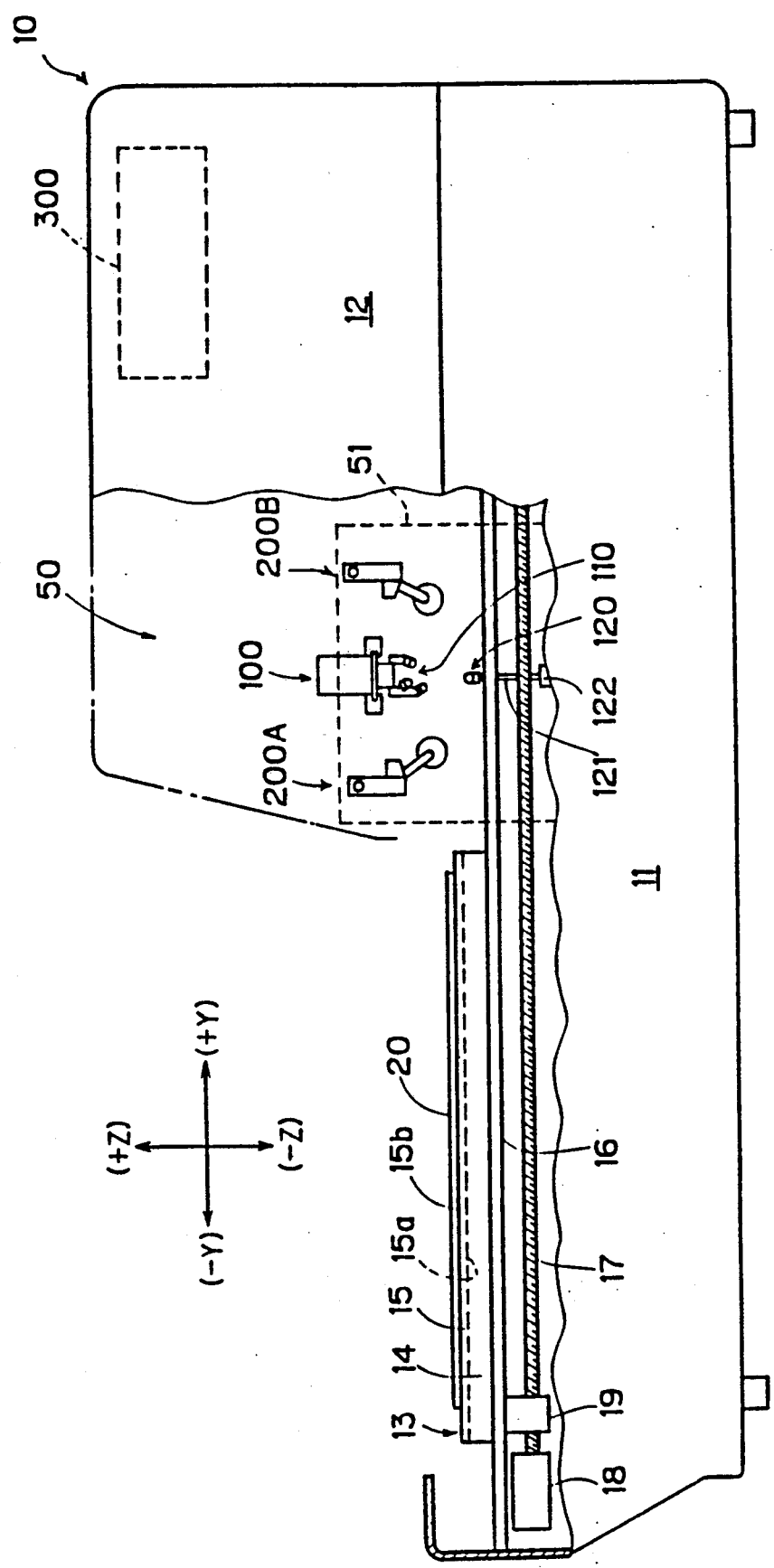
FIG. 1B is a partially fragmented side elevational view of the apparatus shown in FIG. 1A.

FIG. 1A is a fragmented plan view showing a printed circuit board inspecting apparatus 10 in which an image reading system according to a first preferred embodiment of the present invention is incorporated, and FIG. 1B is a side elevational view thereof. The apparatus 10 comprises a lower housing 11 and an upper housing 12, and a movable table 13 is horizontally provided in the vicinity of an upper opening of the lower housing 11. The movable table 13 is formed by a rectangular frame 14 and a glass plate 15 mounted therein, and a bottom surface 15a of the glass plate 15 is coarsely-ground. A printed circuit board 20 is placed on a top surface 15b of the glass plate 15, and supported by the glass plate 15.

Figure 2:
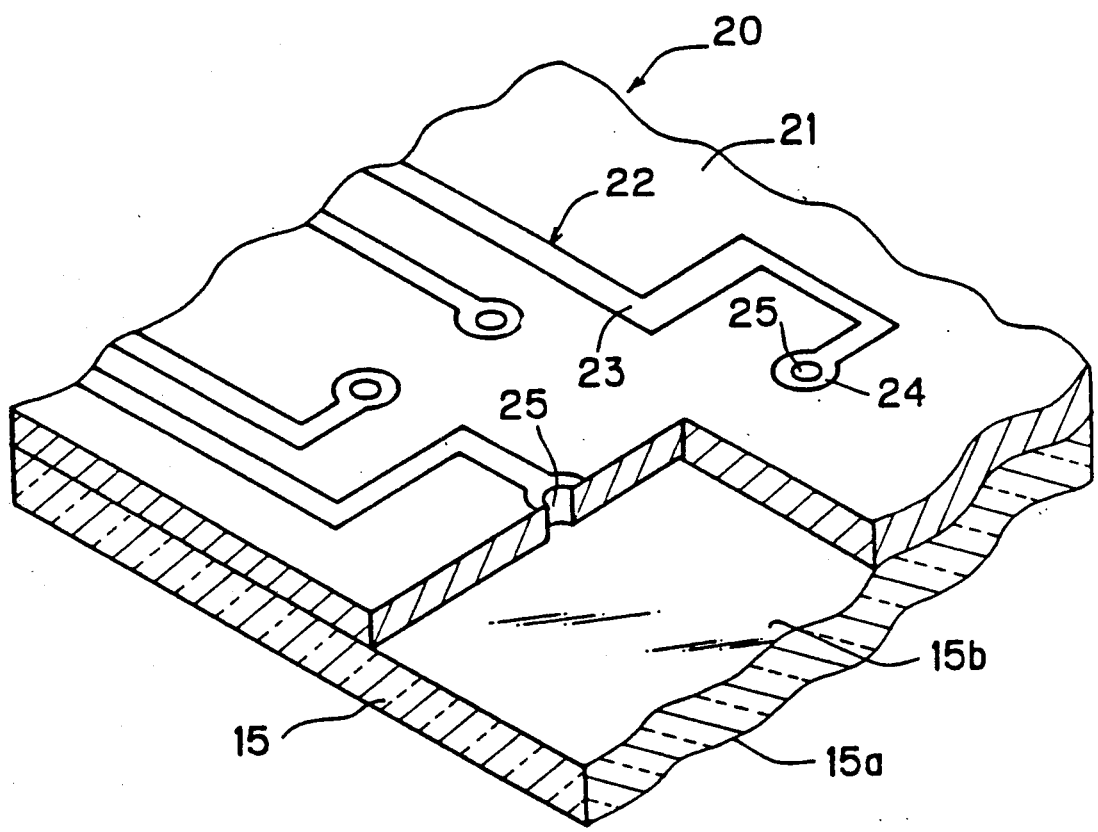
FIG. 2 illustrates an exemplary printed circuit board.

As shown in FIG. 2, the printed circuit board 20 has an insulating base plate 21 which is formed of glass epoxy, and a printed wiring pattern 22 of copper which is formed on one or each surface thereof. The printed wiring patter 22 has a wiring portion 23 and a land 24, and a through hole 25 passing through or penetrating the printed circuit board 20 is formed in the land 24.

Referring again to FIGS. 1A and 1B, the frame 14 is slidable on a pair of guide rails 16, and a ball screw 17 extends in parallel with the guide rails 16. A ball unit 19 fixed to the frame 14 is fitted with the ball screw 17, so that the movable table 13 is moved in horizontal ($\pm Y$) directions when the ball screw 17 is rotated by a motor 18.

On the other hand, an image reading system 50 is provided in the interior of the upper housing 12. An optical head array 100, extending in horizontal ($\pm X$) directions, is arranged in a central upper portion of the image reading system 50. This optical head array 100 comprises eight optical heads H0 to H7, which are supported by a support member 101 at regular intervals. The support member 101 is slidable on a guide member 102 in the directions ($\pm X$), and the guide member 102 is fixed to a pair of side frame members 51a and 51b. The side frame members 51a and 51b are at fixed positions with respect to the housings 11 and 12. The support member 101 is coupled to a motor 103 through a ball nut (not shown) and a ball screw 104. When the motor 103 is rotated, therefore, the optical heads H0 to H7 are movable with the support member 101 in the directions ($\pm X$).

A light source 120 for transmitting illumination is arranged under the optical heads H0 to H7. This light source 120 is formed by a large number of infrared ray LEDs which are arrayed in the directions ($\pm X$), and substantially functions as a linear light source. This light source 120 is supported by support rods 121 and 122 from the side frames 51. Further, another light source 110 for reflective illumination is mounted on lower portions of the optical head H0 to H7. As hereinafter described in detail, the light source 110 comprises three one-dimensional arrays of red LEDs extending in the directions ($\pm X$).

Presser roller mechanisms 200A and 200B are provided in front and at the back of the optical head array 100. The front roller mechanism 200A, comprising eight roller units 210A, is mounted on the side frames 51a and 51b through a shaft 201A. The rear roller mechanism 200B, also comprising eight roller units 210B, is mounted on the side frames 51a and 51b through another shaft 201B. The roller units 200A and 200B have rubber rollers which are supported by swingable arms, and the rubber rollers and the arms are urged by springs. The roller mechanisms 200A and 200B are adapted to press the printed circuit board 20, which are fed under the same, to prevent the circuit board 20 from positional displacement and deflection.

A pair of control switch panels 26 are mounted on top surfaces of both sides of the lower housing 11. These switch panels 26 are provided with identical switch groups, so that the switches can be easily controlled from either side of the housing 11. The upper housing 12 is provided therein with a data processing unit 300 for performing various data processing and operation control.

A-2. Schematic Operation

Before explaining the structure of the inspecting apparatus 10 in detail, a schematic operation of the apparatus 10 is described. First, the printed circuit board 20 is placed on the glass plate 15 in the state shown in FIGS. 1A and 1B. Then either switch panel 26 is operated so that the motor 18 is positively rotated and the printed circuit board 20 is moved in the direction ($+Y$) with the movable table 13. The light sources 110 and 120 are turned on.

When the printed circuit board 20 reaches the position of the image reading system 50 following movement of the table 13, the rollers of the presser roller mechanisms 200A and 200B are rotated following movement of the printed circuit board 20, while pressing the circuit board 20 against the glass plate 15. The optical heads H0 to H7 read images of the wiring pattern 22 (FIG. 2) and the through hole 25 for each scanning line by reflective illumination from the light source 110 and transmitting illumination from the light source 120 respectively. Internal structure of the optical heads H0 to H7 for such reading are described later.

Although the optical heads H0 to H7 are linearly arrayed, it is impossible to read the overall image of the surface of the printed circuit board 20 upon movement in the direction ($+Y$), since gaps are defined between visual fields of the optical head H0 to H7. Therefore, the motor 103 is driven after complete movement of the printed circuit board 20 in the direction ($+Y$), thereby moving the overall optical heads H0 to H7 in the direction ($+X$). The amount of such movement is rendered half the interarray pitch of the optical heads H0 to H7. After such movement, the motor 18 is reversely rotated to move the printed circuit board 20 in the direction ($-Y$), to read the images of the wiring pattern 22 and the through hole 25 by the optical heads H0 to H7.

Consequently, scanning is performed along solid and broken arrows A1 and A2 in FIG. 1A, thereby implementing image reading over the entire surface of the printed circuit board 20. The read images are supplied to the data processing unit 300, which in turn decides whether the wiring pattern 22 and the through hole 25 are defective or non-defective.

A-3. Detail of Optical Heads

Figure 3A:
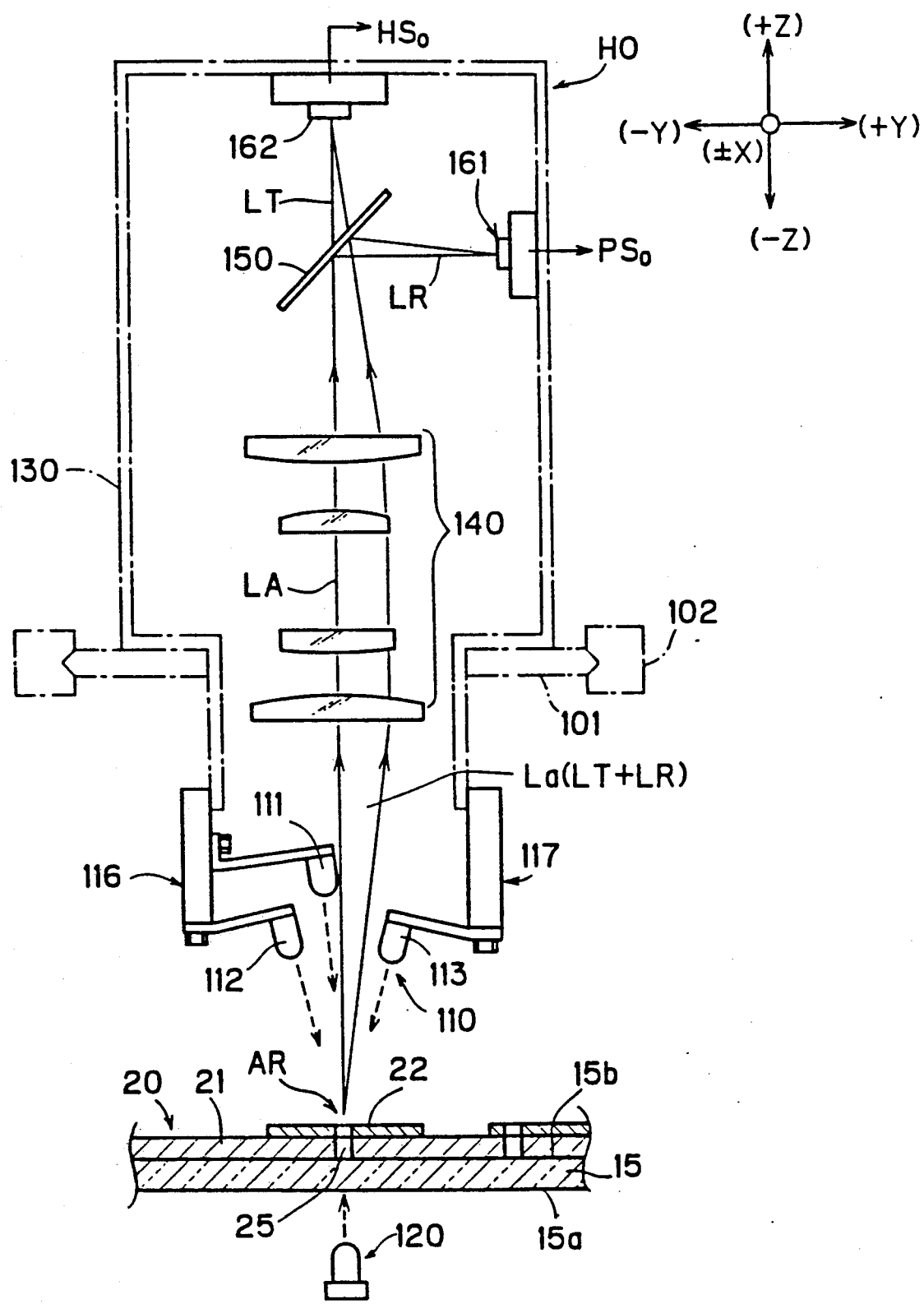
FIG. 3A is a conceptional side elevational view of an optical head according to a first preferred embodiment of the present invention.

FIG. 3A ia a schematical side elevational view showing the internal structure of the optical head H0. While FIG. 3A illustrates only one optical head H0, the other optical heads H1 to H7 have the same structures.

The optical head H0 has a casing 130, and the light source 110 for reflective illumination is suspended by support members 116 and 117 which are mounted on the lower portion of the casing 130. The light source 110 is formed by combination of a light source 111 for image-reading through regular reflection and light sources 112 and 113 for image-reading through irregular reflection, and each of the light sources 111, 112 and 113 is a substantially linear light source which is formed by a one-dimensional array of red LEDs 115 (FIG. 3B) emitting red light of a wavelength $\lambda_1$ (=600 to 700 nm). In the following description, the light source 111 is called as "a light source for regular reflection", while the light sources 112 and 113 are called as "light sources for irregular reflection".

Among these, the light sources 112 and 113 for irregular reflection are arranged at positions considerably separated from an optical axis LA of an imaging lens system 140 which is provided in the optical head H0, while the light source 111 for regular reflection is provided in such a position that its end surface is in contact with the optical axis LA. As hereinafter described, the imaging lens system 140 is adapted to form the images of the wiring pattern 22 and the through hole 25 of the printed circuit board 20 on CCD linear image sensors 161 and 162 respectively. The light sources 112 and 113 for irregular reflection are arranged in the exterior of the visible field or the angular aperture for the imaging, while the light source 111 for regular reflection is arranged in a part of the angular aperture.

Light emitted from the light sources 111, 112 and 113 is applied toward an inspected area AR of the top surface of the printed circuit board 20, which is currently located immediately under the optical head H0. The light source 111 for regular reflection and the light sources 112 and 113 for irregular reflection are provided for reflective illumination for the reason that it is preferable to utilize both of regular reflection and irregular reflection from the wiring pattern 22 in order to correctly catch the image thereof, since the surface of the wiring pattern 22 does not necessarily define a mirror finished surface. The light sources 111, 112 and 113 are shaped on the imaging lens system 140 sides, i.e., in the upper sides of FIGS. 1A and 1B.

On the other hand, the light source 120 for transmitting illumination is formed by a one-dimensional array of red LEDs 125 (FIG. 3B) generating infrared light of a wavelength $\lambda_2$ (=700 to 1000 nm). This light source 120 is provided on a line perpendicularly intersecting with the optical axis LA of the imaging lens system 140. This light source 120 emits the infrared light toward an area of the back surface of the printed circuit board 20 corresponding to the back side of the inspected area Ar in a direction (+Z).

The red light applied to the inspected area AR from the light sources 111, 112 and 113 for reflective illumination is reflected by the inspected area AR. In the infrared light emitted from the light source 120 for transmitting illumination, part directed to the through hole 25 is penetrated or transmitted through the through hole 25. The reflected light and the transmitted light are spatially overlapped to become compound light, which in turn is directed to the optical head H0.

Figure 4A:
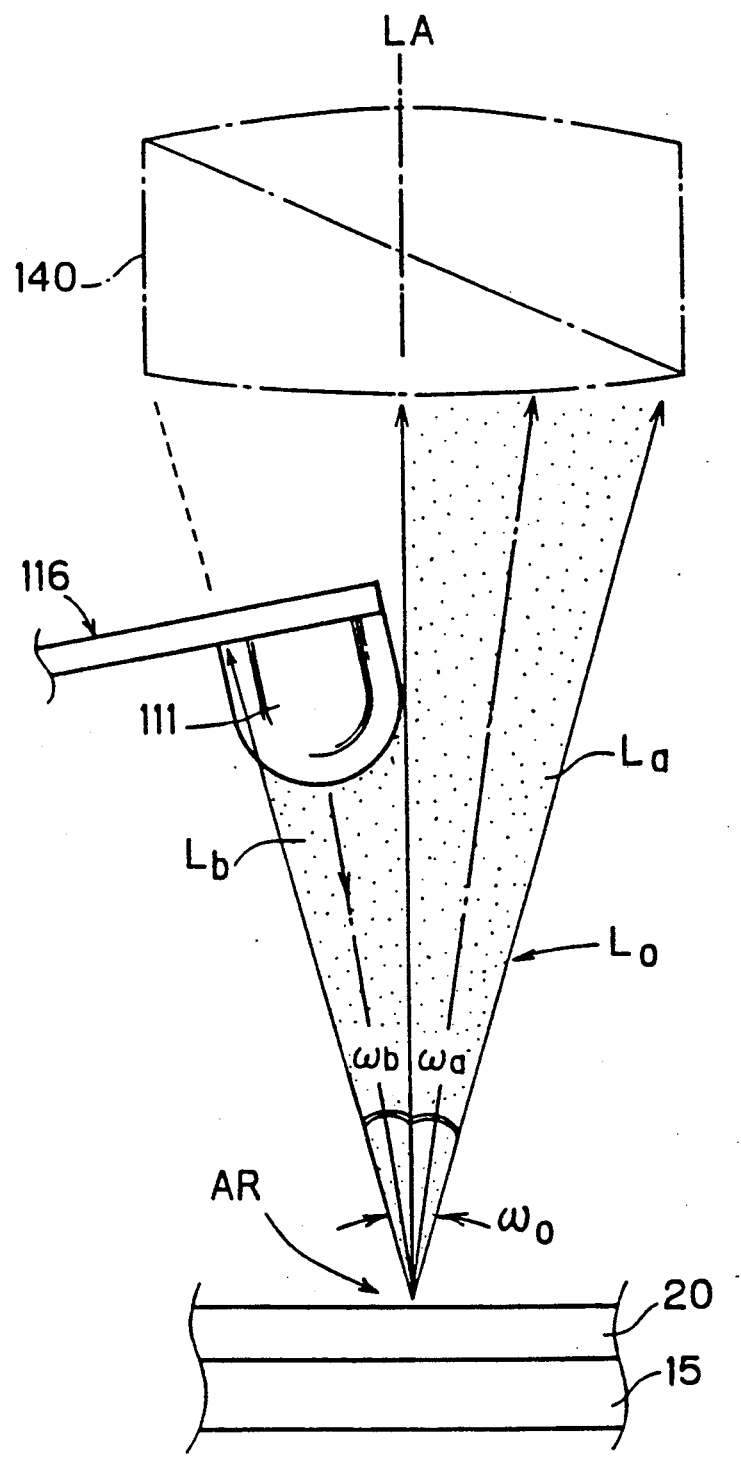
FIG. 4A illustrates relation between the position of arrangement of a light source for regular reflection and incident luminous flux in an imaging lens system.

Referring to FIG. 4A, there is shown luminous flux $L_O$ outputted from the inspected area AR of the printed circuit board 20 and traveling toward a range of an entrance pupil of the imaging lens system 140. Only a part $L_a$ of the luminous flux $L_O$, which corresponds to half luminous flux $L_O$, reaches the imaging lens system 140 and another part $L_b$ corresponding to the remaining half is eclipsed or blocked by the light source 111 and the support member 116. Assuming that the parts $L_a$ and $L_b$ are called as "effective luminous flux" and "ineffective luminous flux", therefore, each of the projection solid angle (the incoming angle of the compound light in the imaging lens system 140) $\omega_a$ of the effective luminous flux $L_a$ and the projection solid angle $\omega_b$ of the ineffective luminous flux $L_b$ is half the projection solid angle (the angular aperture) $\omega_O$ of the luminous flux $L_O$. In other words, the following equations (1) to (4) hold:

$$\omega_a + \omega_b = \omega_O \quad (1)$$

$$\omega_a = \alpha \cdot \omega_O \quad (2)$$

$$\omega_b = (1-\alpha) \cdot \omega_O \quad (3)$$

$$\alpha = \tfrac{1}{2} \quad (4)$$

As shown in FIG. 3A, the effective luminous flux $L_a$ enters a cold mirror 150 through the imaging lens system 140. The cold mirror 150 is adapted to transmit only infrared light. Therefore, the red light contained in the effective luminous flux $L_a$ (i.e., the reflected light LR from the surface of the printed circuit board 20) is reflected by this mirror 150 to progress in the direction (+Y), and imaged on a photos-detective plane of the first CCD linear image sensor 161. Further, the infrared light contained in the effective luminous flux $L_a$ (i.e., the transmitted light LT through the through hole 25) is transmitted through the mirror 150 and imaged on a photo-detective plane of the second CCD linear image sensor 162.

These CCD linear image sensors 161 and 162 have CCD photo-electric converter cells which are one-dimensionally arrayed in the directions (±X). Therefore, the first linear image sensor 161 detects a one-dimensional image of the surface of the printed circuit board 20 through the reflective illumination, while the second linear image sensor 162 detects a one-dimensional image of the through hole 25 through the transmitting illumination. The printed circuit board 20 and the optical head array 100 are relatively moved by the moving mechanism shown in FIGS. 1A and 1B, whereby respective areas of the printed circuit board 20 are scanned and two-dimensional images of the wiring pattern 22 and the through hole 25 are obtained for respective areas on the printed board 20.

Figure 5A:
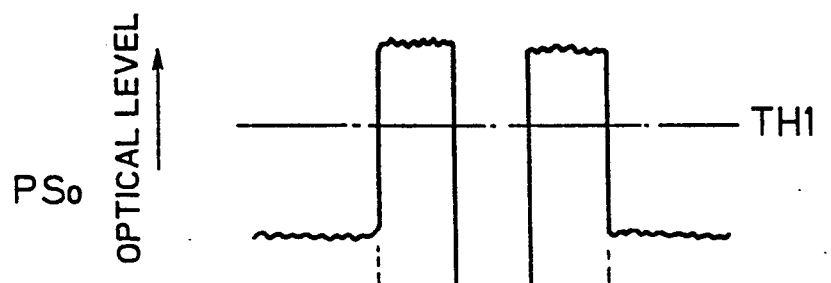
FIGS. 5A and 5B are waveform diagrams showing image signals obtained by the system of the first preferred embodiment and binarization processing therefor.
Figure 5B:
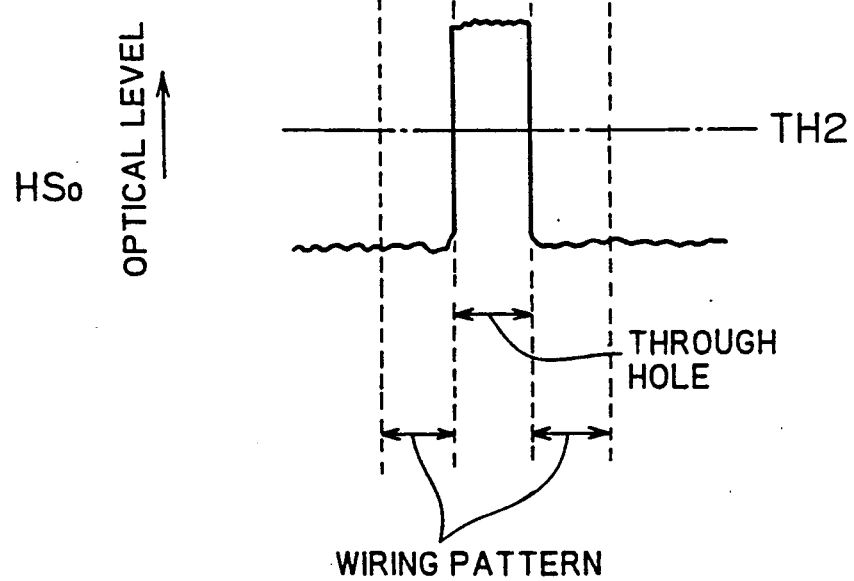

Image signals obtained in the linear image sensors 161 and 162 are digitalized by circuits described below, and thereafter binarized using threshold values TH1 and TH2, as shown in FIGS. 5A and 5B. FIG. 5A shows an exemplary image signal $PS_0$ which is obtained in the first linear image sensor 161, and FIG. 5B shows an exemplary image signal $HS_0$ which is obtained in the second linear image sensor 162.

Figure 3B:
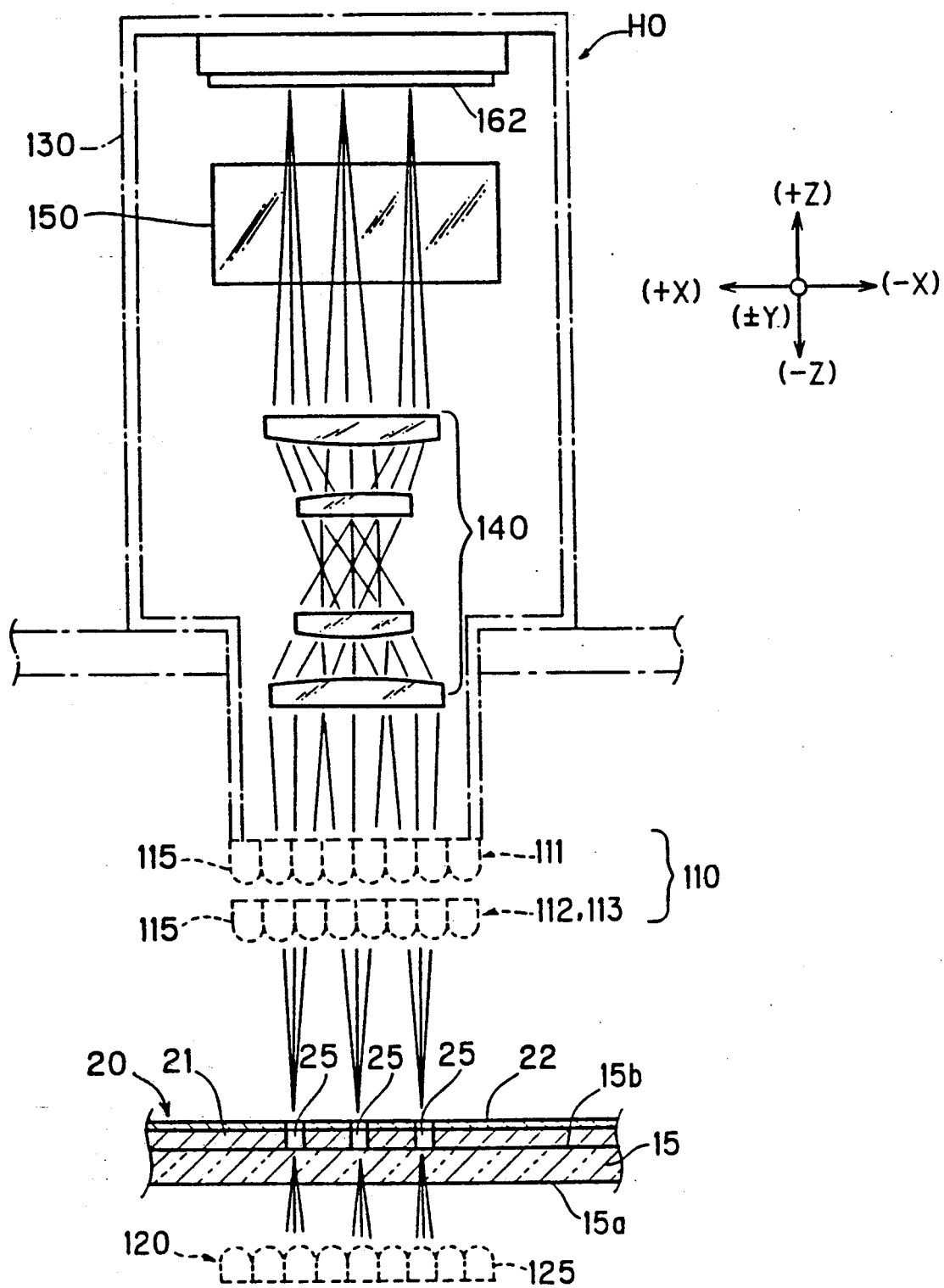
FIG. 3B is a conceptional front elevational view of the optical head shown in FIG. 3A.

FIG. 3B is a typical front elevational view of the optical head H0 shown in FIG. 3A, and the first linear image sensor 161 is omitted in FIG. 3B for convenience of illustration. Optical paths in the optical head H0 are shown only as to the light transmitted through the through hole 25. In this embodiment, a telecentric lens system, which is telecentric on both sides being close to the printed circuit board 20 and the linear image sensors 161 and 162, is employed as the imaging lens system 140. Therefore, an imaging optical axis of the transmitted light from each through hole 25, which is in the visual field of this lens system 140, is parallel to the optical axis LA of the lens system 140 itself in both of the object side and the image-detection side of the lens system 140.

Figure 27:
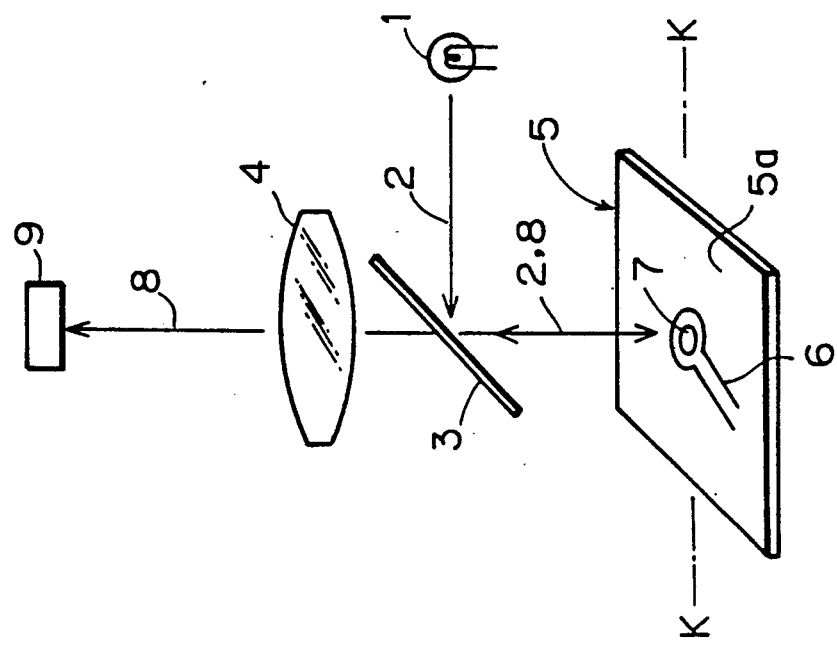
FIG. 27 is a principle diagram of a conventional image reading system.

The image reading system 50 having the aforementioned structure has the following advantages:

(1) Half the light outputted from the surface of the printed circuit board 20 toward the entrance pupil of the lens system 140 is imaged on the linear image sensors 161 and 162. In the prior art shown in FIG. 27, on the other hand, the light 8 reaching the image sensor 9 is $\frac{1}{4}$ of the light 2 from the light source 1, as described above.

Figure 6A:
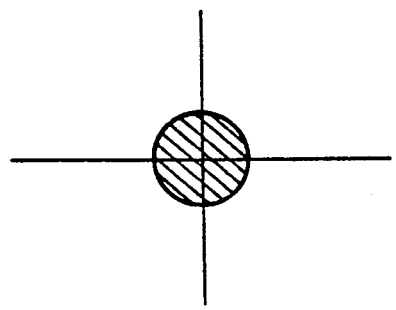
FIGS. 6A to 6C are conceptional diagrams showing ranges of incidence upon imaging lens systems and incident light intensity levels as to the prior art, the first preferred embodiment and an improvement to be compared with the first preferred embodiment, respectively.
Figure 6B:
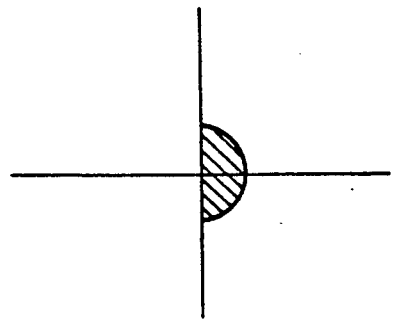

FIGS. 6A and 6B are schematical diagrams for the prior art and the embodiment, respectively, showing the range in which the light from the printed circuit board is actually incident within the entrance pupil of the imaging lens system and the transmitted optical density thereof. Referring to FIG. 6A corresponding to the prior art shown in FIG. 27, the light is incident upon the overall area of the entrance pupil while the transmitted optical density thereof is $\frac{1}{4}$ of or less than the optical density of the light generated in the light source 1. Referring to FIG. 6B for the embodiment, on the other hand, only half the entrance pupil is utilized, while the transmitted optical density thereof is four times that of the prior art. In this comparison, only the light source 111 for regular reflection is considered as to the embodiment.

Therefore, the intensity of the light incident upon the linear image sensor 161 in the embodiment is twice that of the light incident upon the image sensor 9 in the prior art, and it is possible to obtain images at a high contrast which are hardly influenced by noises.

Figure 7:
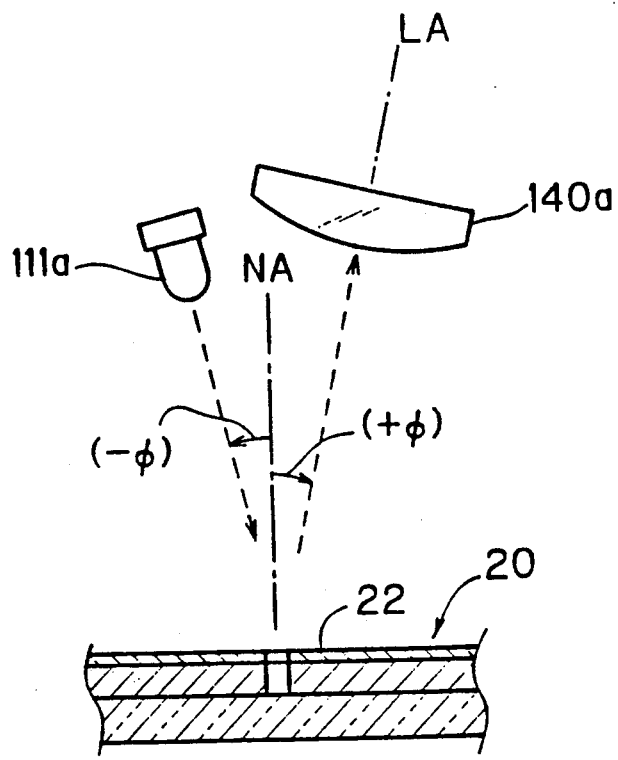
FIG. 7 is an explanatory diagram showing arrangement in the improvement.
Figure 8:
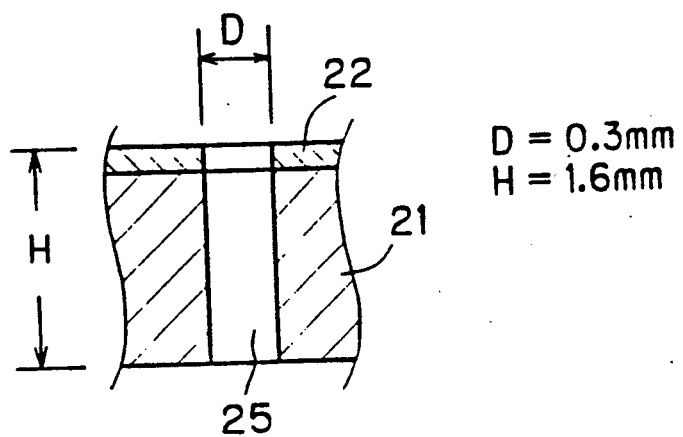
FIG. 8 is an explanatory diagram of a mini via hole.

As shown in FIG. 7, also conceivable is a technique of arranging an optical axis LA of an imaging lens system 140a with inclination from a normal direction NA of a printed circuit board 20 by an angle $(+\phi)$ while inclining a light source 111a for regular reflection from the normal direction NA by an angle $(-\phi)$. When the value of the angle $\phi$ is increased to some extent in this case, reflected light from the printed circuit board 20 is incident upon the imaging lens system 140a without being eclipsed by the light source 111a, and the intensity of incident light upon a linear image sensor is doubled as compared with the embodiment.

Figure 6C:
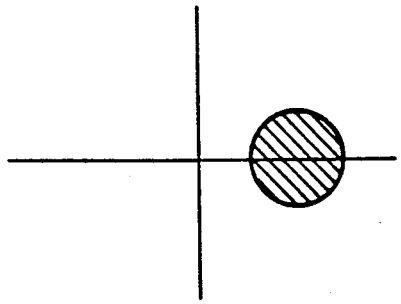

In this case, however, image detection is performed in a direction inclined from the normal direction NA, and no image detection is performed just on an inspected area. FIG. 6C schematically shows such circumstances, and displacement of a photo-detective range from a cross point in FIG. 6B expresses such inclination. Due to such inclination, it is impossible to attain focusing entirely over the inspected area, whereby blurring or distortion is caused in a detected image of the wiring pattern 22 and detection accuracy therefor is reduced. On the other hand, no such problem is caused in the arrangement of the embodiment.

The mirror 150 arranged above the imaging lens system 140 in the embodiment is not a half mirror, but luminous flux, which is incident upon this mirror 150 within regularly reflected light, is substantially entirely reflected, whereby the light intensity is not reduced by half at the mirror 150.

(2) The appearance inspection of the circuit board 20 can be performed at a high speed since the images of the wiring pattern 22 and the through hole 25 are simultaneously obtained. Further, since the imaging lens system 140 is commonly employed in image detection of the wiring pattern 22 and that of the through hole 25, there is no need to provide a plurality of imaging lens systems in parallel in each optical head.

(3) Since the images of the wiring pattern 22 and the through hole 25 are separately detected by the linear image sensors 161 and 162 as shown in FIGS. 5A and 5B, the threshold value levels TH1 and TH2 can independently be set at optimum values in no consideration of interrelation therebetween. Consequently, it is possible to correctly detect the respective images even if photoreceptive levels of the respective images fluctuate.

(4) The imaging lens system 140 is formed by a telecentric lens system, so that it is possible to correctly detect an image of a through hole, such as a mini via hole, having a small diameter. The reason for this is as follows:

FIG. 6 illustrates an example of a mini via hole in which the ratio (aspect ratio) of a length (depth) H to a diameter D is given as:

$$H/D = 1.6 \text{ mm}/0.3 \text{ mm} = 5.3 \tag{5}$$

Figure 9A:
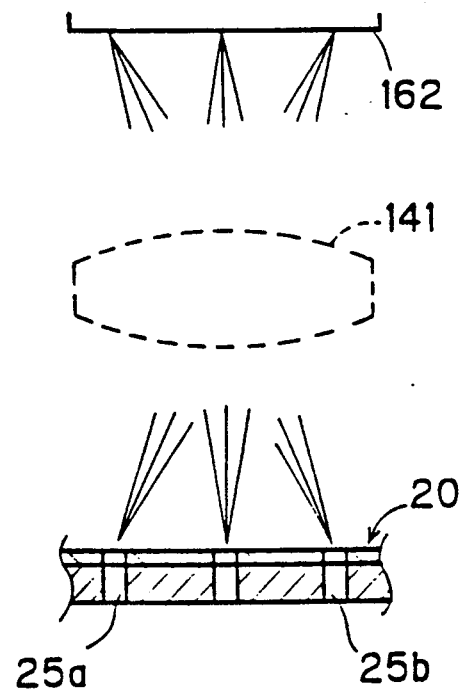
FIGS. 9A and 9B are explanatory diagrams of a non-telecentric lens system and a telecentric lens system, respectively.

When a non-telecentric lens system 141 is employed as shown in FIG. 9A, respective hole spaces in holes 25a and 25b separated from the optical axis of the lens system are partially shaded from the light source for transmitting illumination, and, as shown in FIG. 10A, hole images 25A and 25B corresponding to the holes 25a and 25b are partially lost in image signals obtained therefrom.

Figure 9B:
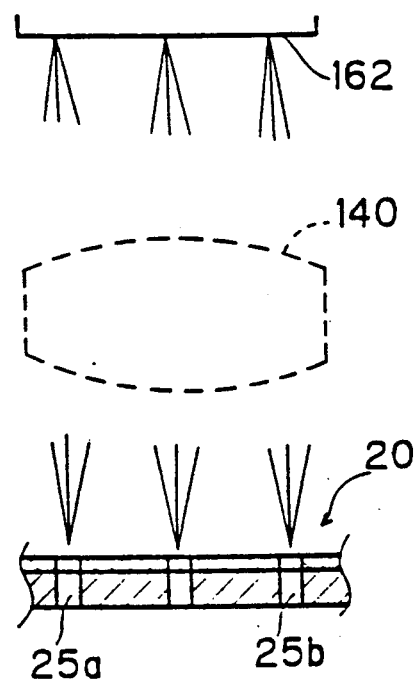

When the telecentric lens system 140 is employed as in the embodiment, on the other hand, it is possible to correctly catch images of holes 25a and 25b which are separated from its optical axis (FIGS. 9B and 10B).

(5) Since the bottom surface 15a (FIG. 2) of the glass plate 15 is coarsely ground, the light from the light source 120 for transmitting illumination is uniformly applied to the back surface of the circuit board 20. Therefore, the photo-level on the image of the through hole 25 is uniformalized.

A-4. Electrical Structure

Figure 11B:
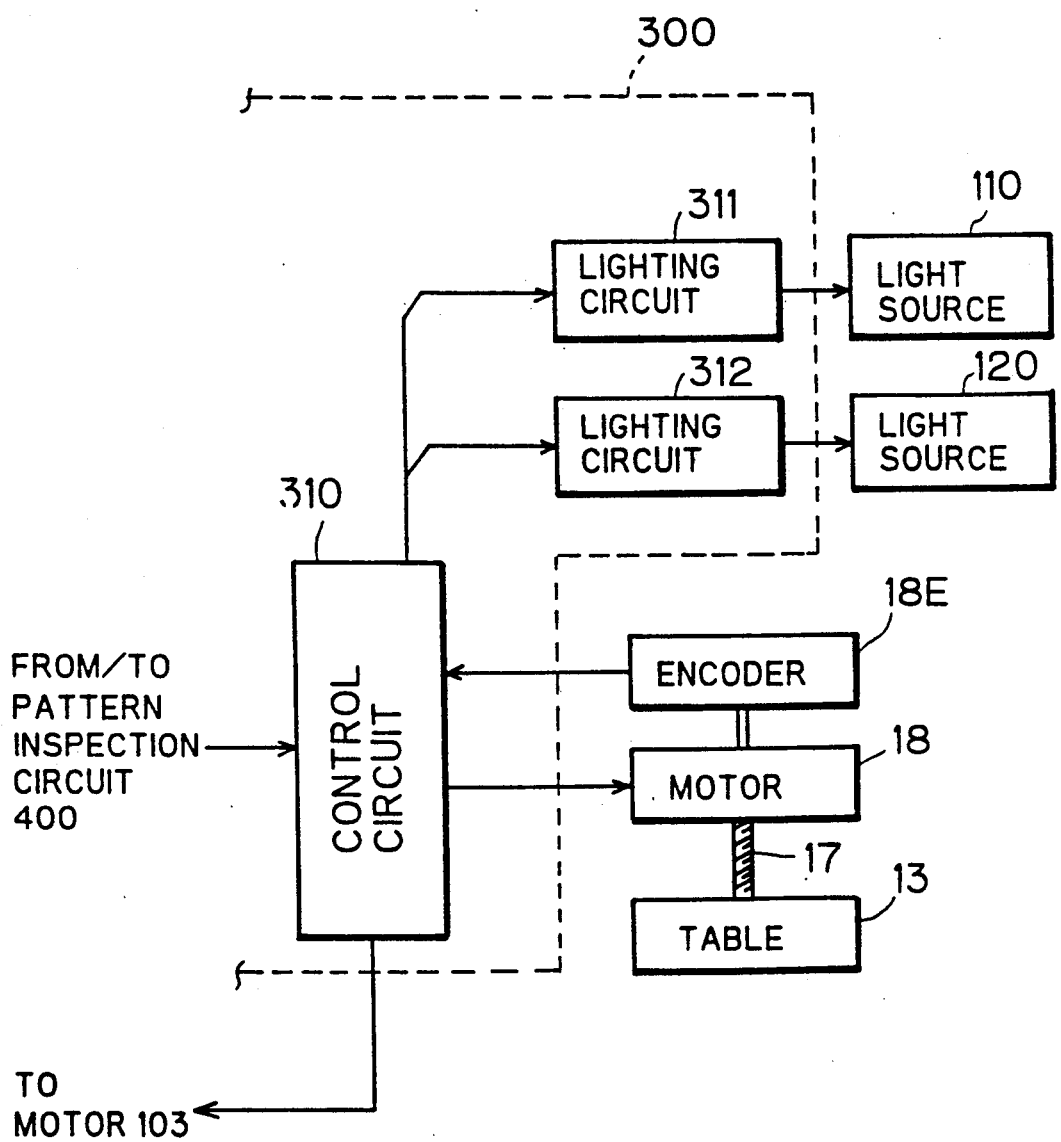

FIG. 11A as combined with FIG. 11B is a block diagram showing an electrical structure of this embodiment. wiring pattern image signals $PS_0$ to $PS_7$ and through hole image signals $HS_0$ to $HS_7$ obtained from the optical heads H0 to H7 are converted to digital signals by A-D converters 301, and thereafter supplied to binarizing circuits 302 and 303.

Figure 11C:
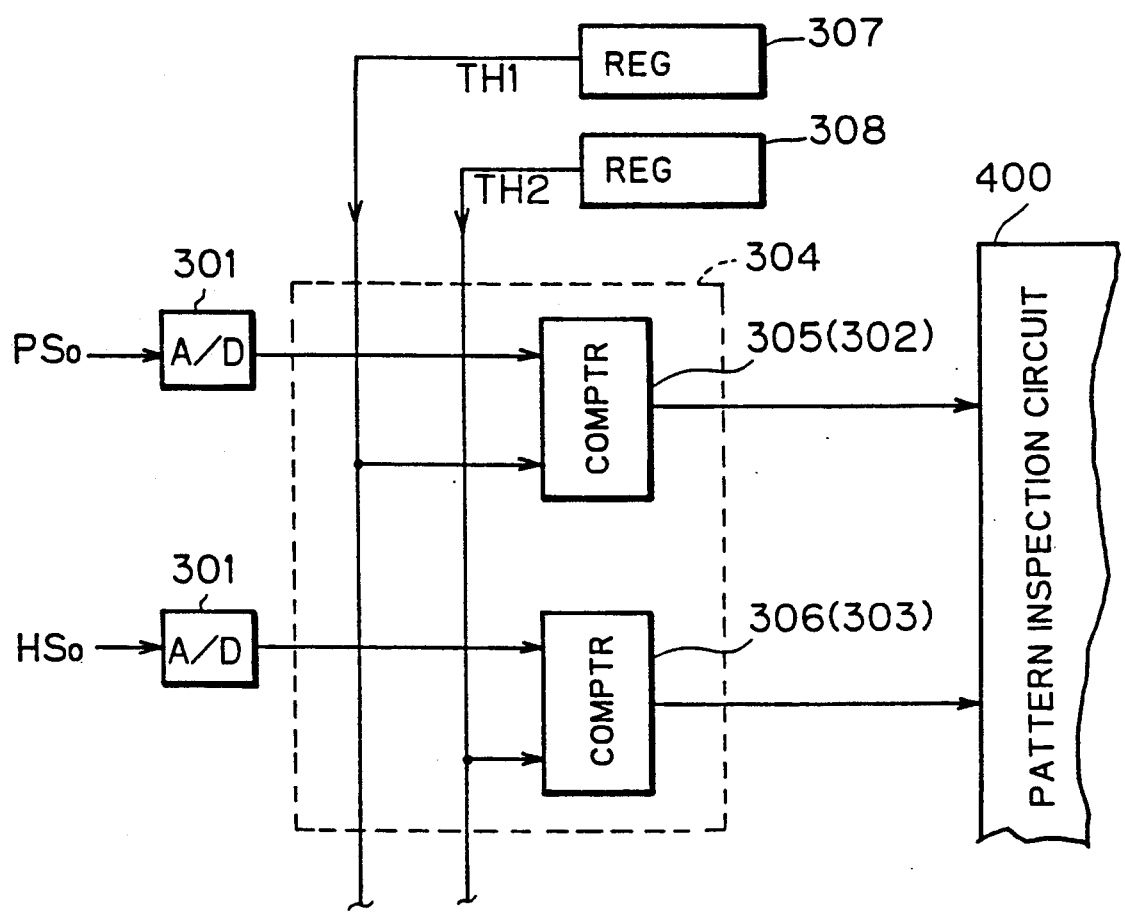

FIG. 11C shows combination 304 of the binarizing circuits 302 and 303 corresponding to the optical head H0 in detail. The binarizing circuits 302 and 303 are formed by comparators 305 and 306, and the threshold values TH1 and TH2, which are held by registers 307 and 308, are supplied to the comparators 305 and 306, respectively. The comparators 305 and 306 compare the threshold values TH1 and TH2 with the digitalized image signals $PS_0$ and $HS_0$ (see FIGS. 5A and 5B) respectively, to output binarized signals, which go high when the levels of the signals $PS_0$ and $HS_0$ are higher than the threshold values TH1 and TH2 while going low when the former are lower than the latter. The binarizing circuits 302 and 303 corresponding to the other optical heads H1 to H7 have similar structures, and the threshold values TH1 and TH2 from the registers 307 and 308 are commonly used for the respective pairs of the binarizing circuits 302 and 303.

Referring again to FIGS. 11A and 11B, the binarized image signals thus obtained are supplied to a pattern inspection circuit 400. The pattern inspection circuit 400 constructs two-dimensional images of the wiring pattern 22 and the through hole 25 on the basis of these image signals, and determines whether the wiring pattern 22 and the through hole 25 are defective or nondefective in accordance with prescribed determination rule.

The data processing unit 300 is also provided with a control circuit 310. The control circuit 310 supplies turn-on/off instructions to the light sources 110 and 120 through lighting circuits 311 and 312, and outputs driving control signals to the motors 18 and 103. The motor 18 is provided with a rotary encoder 18E, so that a motor rotation angle signal generated therein is delivered to the control circuit 310. This rotation angle signal defines data processing timing.

According to the aforementioned structure, the optical inspecting apparatus 10 shown in FIGS. 1A and 1B accurately executes appearance inspection of the printed circuit board 20.

A-5. Modification of First Preferred Embodiment (1) The light source 111 for regular reflection may be arranged on a part of each angular aperture of the optical heads H0 to H7, and may not necessarily be in contact with the optical axis LA of the imaging lens system 140. Namely, the value of the parameter $\alpha$ in the equations (1) to (3) can be selected in various ways in the following range:

$$0 < \alpha < 1 \qquad (6)$$

Figure 4B:
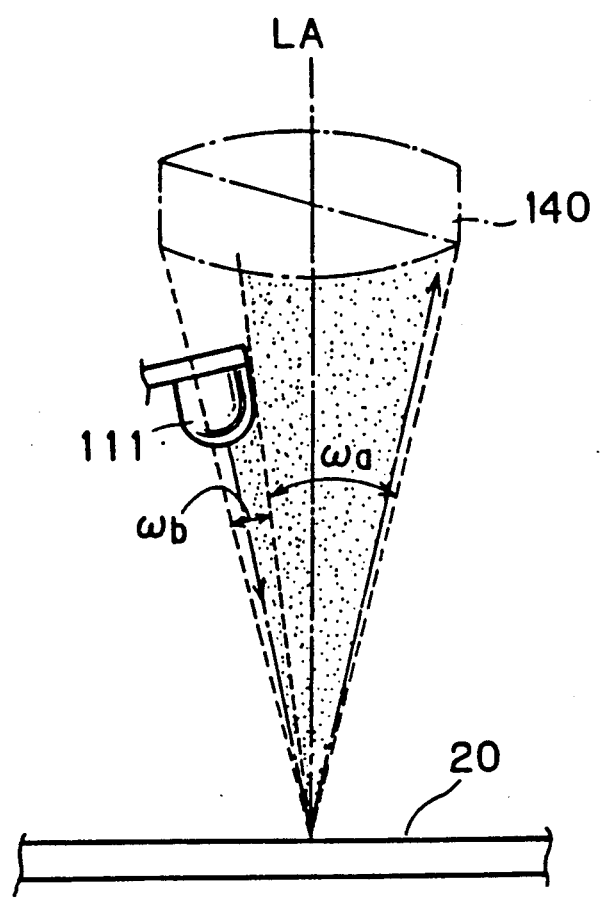
FIG. 4B illustrates incident luminous flux in an imaging lens system in a modification of the first preferred embodiment.

When the parameter $\alpha$ is taken at a relatively large value, the effective angular apertures of the optical heads H0 to H7 are widened (FIG. 4B). However, since the light from the light source 111 is incident upon the surface of the printed circuit board 20 at a shallow angle in this case, the reflection angle of regular reflection thereof also becomes shallow and the intensity of reflected light (effective luminous flux) incident upon the imaging lens system 140 is inevitably reduced. When the parameter $\alpha$ is taken at a relatively small value, the reflection angle is increased but the effective angular apertures are narrowed, whereby the intensity of the effective luminous flux is likewise reduced.

The intensity of the effective luminous flux can be considered as being proportionate to the product of the solid angles $\omega_a$ and $\omega_b$ in the equations (1) to (3). The solid angle $\omega_a$ expresses the width of the effective angular aperture of the imaging lens system 140, and the solid angle $\omega_b$ influences a reflection angle in reflection of the light, emitted from the light source 111, by the surface of the printed circuit board 20. Therefore, intensity $Q_e$ of the effective luminous flux can be written as follows, using a proportional constant C:

$$Q_e = C \cdot \omega_a \omega_b \qquad (7)$$

The following equation (8) is obtained using the theorem that an arithmetic mean is equal to or more than a geometric mean:

$$Q_e = C \cdot \omega_a \omega_b \leq C \cdot (\omega_a + \omega_b)^2 / 4 \qquad (8)$$

Using the condition of the equation (1), the equation (9) is obtained:

$$Q_e \leq C \cdot \omega_0^2 / 4 \qquad (9)$$

where $Q_e$ takes the maximum value $C \cdot \omega_0^2 / 4$ when:

$$\omega_a = \omega_b \qquad (10)$$

For this reason, the embodiment shown in FIG. 4A is constructed so that the condition $\alpha = \frac{1}{2}$ and the equation (10) hold.

Figure 12:
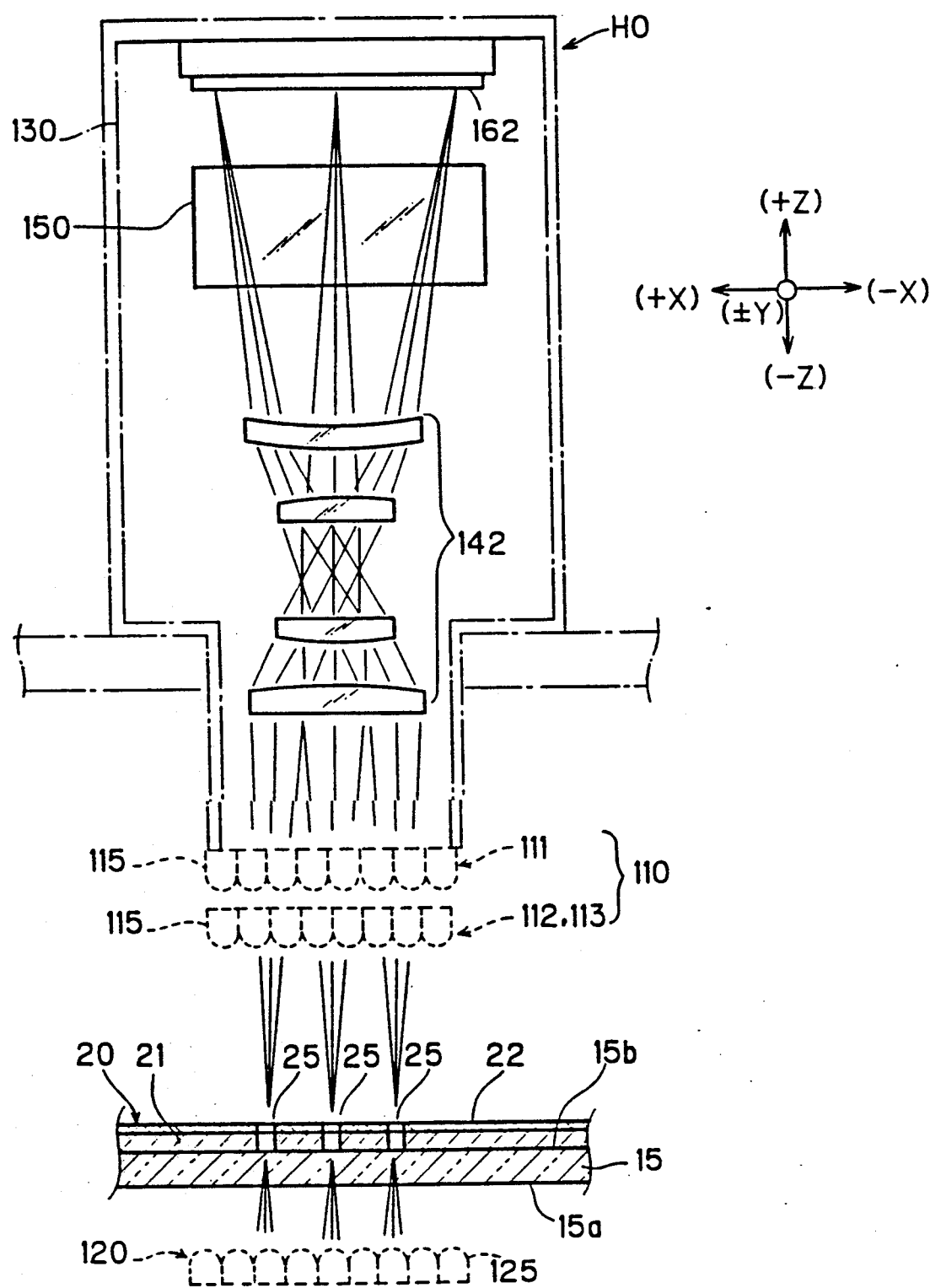
FIG 12 is a conceptional front elevational view of a modification of the first preferred embodiment.

(2) FIG. 12 is a typical front elevational view showing a modification of the optical head H0, which is illustrated in a manner similar to FIG. 3B. In the optical head H0 as modified, a lens system which is telecentric only on the object side (i.e., a side of the printed circuit board 20) is employed as an imaging lens system 142. It is possible to correctly catch the image of a through hole 25 also by such a structure.

(3) The light emitted from the light source for reflective illumination and that emitted from the light source for transmitting illumination may be different in wavelength from each other, and it is not requisite to combine the red light with the infrared light as in the aforementioned embodiment.

For example, visible light having a first wavelength may be employed for the light source 110 for reflective illumination in FIGS. 3A and 3B, and visible light having a second wavelength may be employed for the light source 120 for transmitting illumination. The first and second wavelengths are different from each other. In this case, a dichroic mirror can be employed in place of the cold mirror 150. Such a dichroic mirror is implemented by a mirror which reflects the light of the first wavelength and transmits the light of the second wavelength.

As to each of the light sources 110 and 120, combination of a white light source and a color filter may be employed.

While the invention has been shown and described in detail, the foregoing description is in all aspects illustrative and not restrictive. It is therefore understood that numerous modifications and variations can be devised without departing from the scope of the invention.

B. Second Preferred Embodiment

Figure 13:
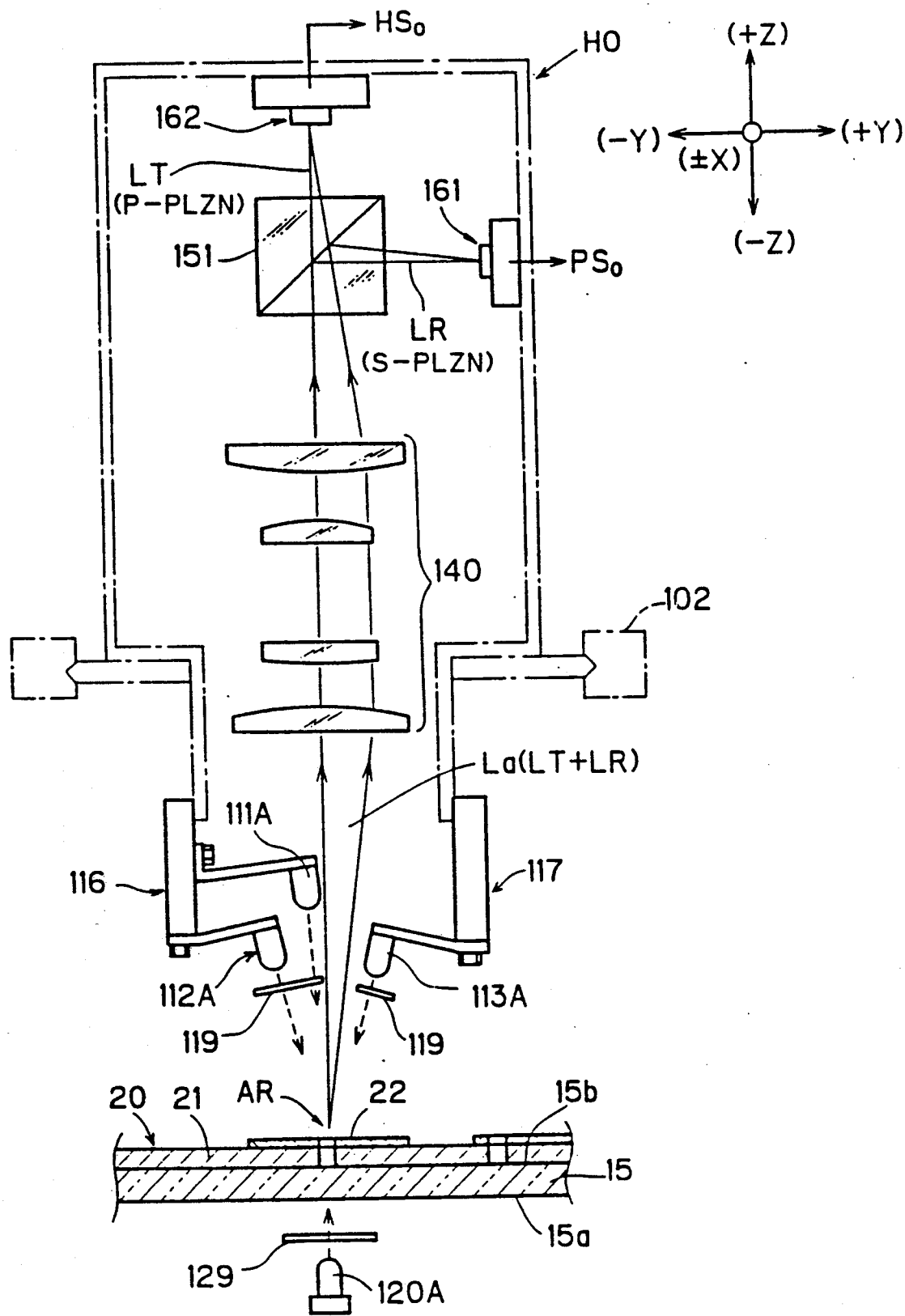
FIG 13 is a conceptional side elevational view of an optical head according to a second preferred embodiment of the present invention.

FIG. 13 illustrates an optical head H0 according to a second preferred embodiment of the present invention, which optical head H0 is employable in the image reading system 50 shown in FIGS. 1A and 1B. In this optical head H0, combination of white light sources 111A, 112A and 113A and an S-wave polarizing plate 119 is employed as a light source system for reflective illumination. Therefore, the reflective illumination light is an S-wave light, i.e., a light wave whose electric field vector is in the directions ($\pm X$). The polarizing plate 119 is supported from the optical head H0 side by a support member (not shown).

On the other hand, a light source system for transmitting illumination is formed by combination of a white light source 120A and a P-wave polarizing plate 129, and the P-wave polarizing plate 129 is supported from the white light source 120A side by a support member (not shown). Therefore, transmitting illumination light is a P-wave light, i.e., light wave whose electric field vector is in an XZ plane.

Each illumination light is applied toward a printed circuit board 20 similarly to the case of FIG. 3A, and compound light from the circuit board 20 is incident upon a polarized beam splitter 151 through a telecentric lens system 140. The polarized beam splitter 151 reflects the S-wave and transmits the P-wave. Therefore, S-polarized reflected light LR containing image information of a wiring pattern 22 is imaged on a photoelectric converter plane of a linear image sensor 161, while P-polarized transmitted light LT containing image information of a through hole 25 is imaged on a photoelectric converter plane of another linear image sensor 162. The remaining structure is identical to that of FIG. 3A and the light source 112A is in contact with the optical axis of the imaging lens system 140.

Also in this embodiment, respective images of the wiring pattern 22 and the through hole 25 are simultaneously detected by the separate linear image sensors 161 and 162, whereby an effect similar to that of the system shown in FIG. 3A is attained. Alternatively, the light for reflective illumination may be P-polarized, and the light for transmitting illumination may be S-polarized. When a light source, such as a laser source, emitting light which is polarized in a specific direction is employed, no polarizing plate may be employed.

C. Third Preferred Embodiment

C-1. Construction

Figure 14A:
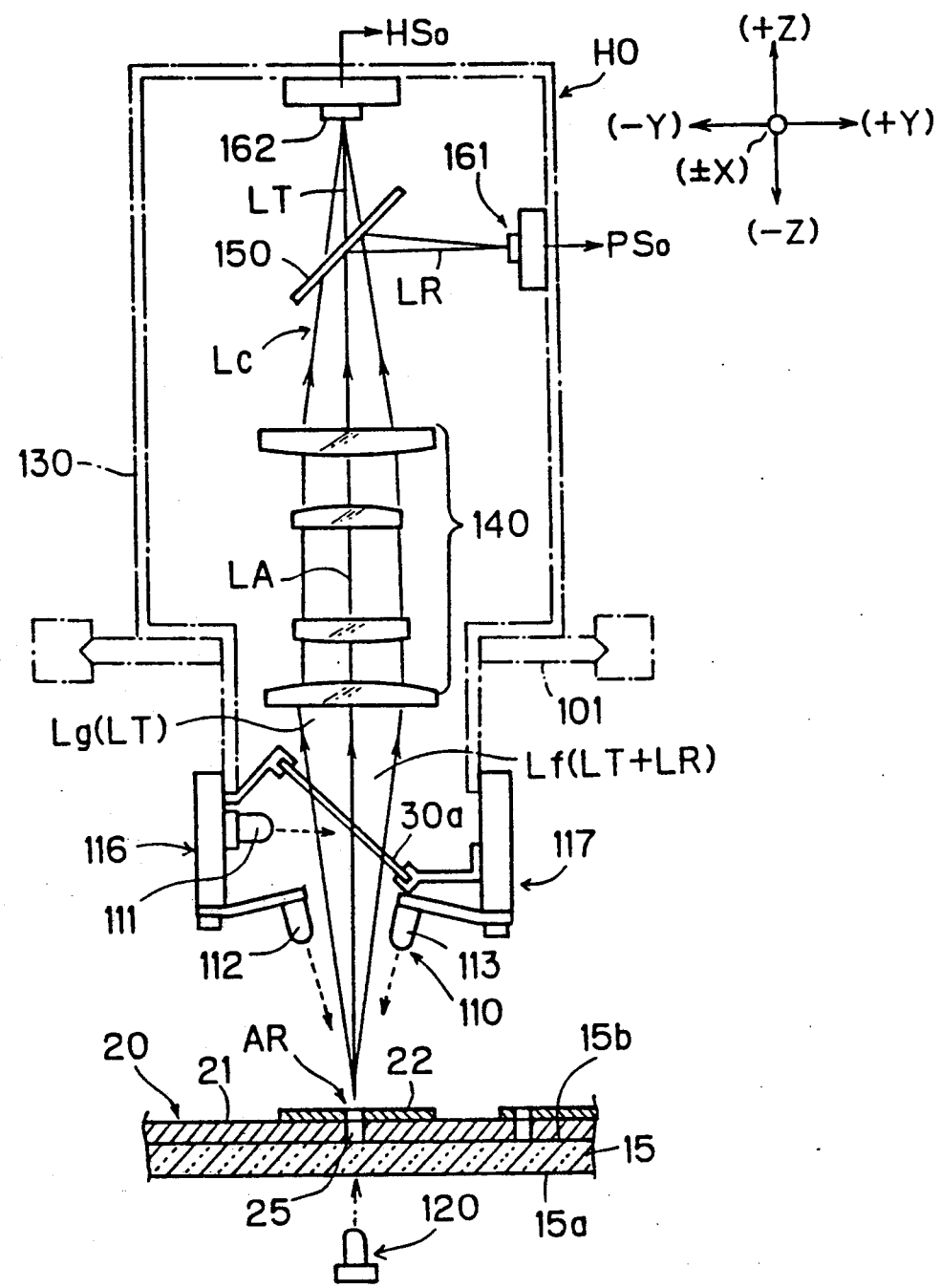
FIG. 14A is a conceptional side elevational view of an optical head according to a third preferred embodiment of the present invention.
Figure 14B:
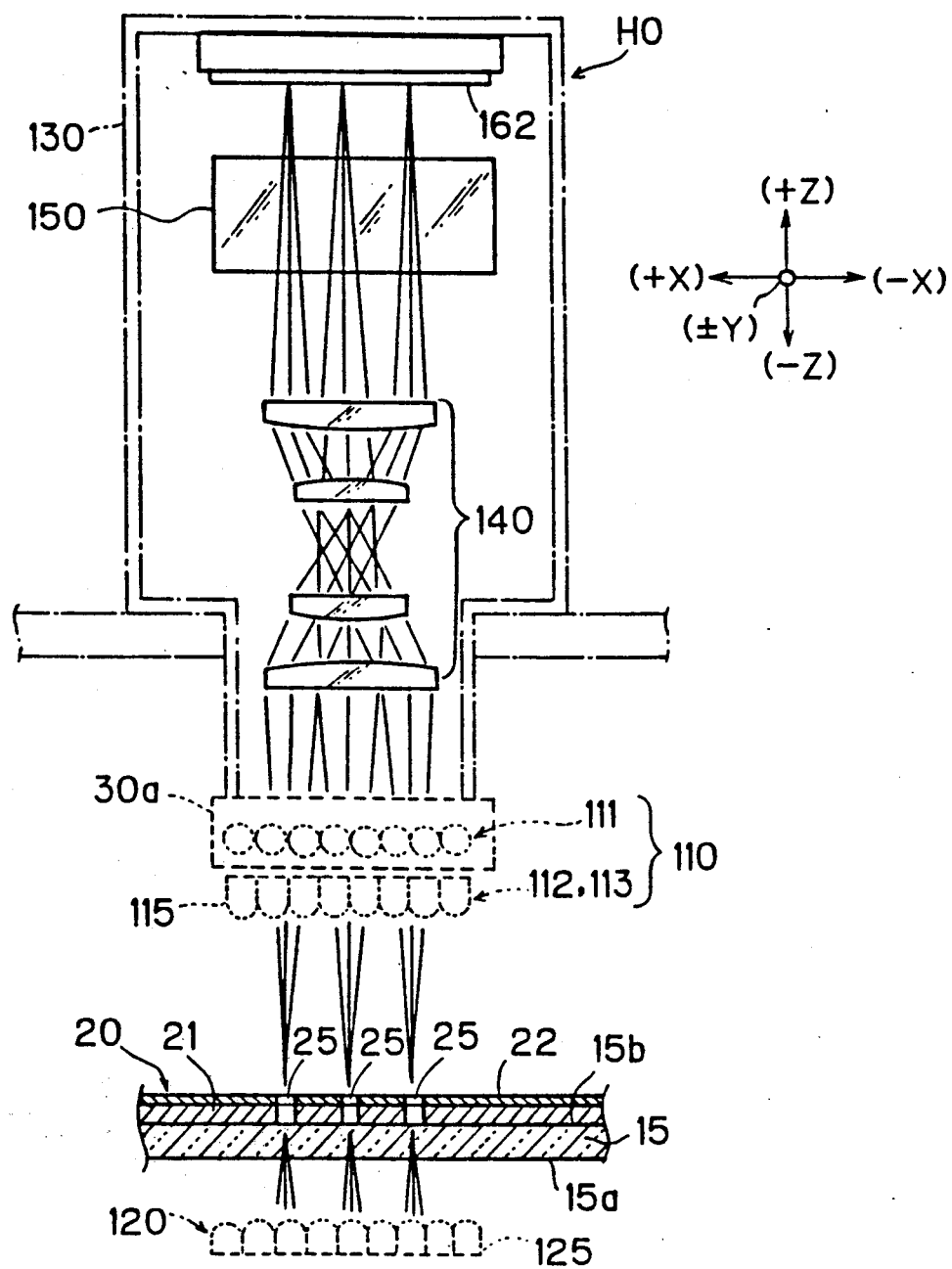
FIG. 14B is a conceptional front elevational view of the optical head shown in FIG. 14A.

FIG. 14A is a conceptional side elevational view of an optical head H0 according to a third preferred embodiment of the present invention and FIG. 14B is a conceptional front elevational view of the optical head H0 shown in FIG. 14A. Although the optical head H0 in FIGS. 14A and 14B is comparable to the optical head shown in FIG. 3A and 3B in many points, the former has a characteristic structure as follows:

The optical head H0 in FIGS. 14A and 14B, the light source 111 for regular reflection is attached to the supporting member 116 in lateral direction (+Y) and is out of the angular aperture of the imaging lens system 140. The arrangement of the other light sources 112, 113 and 120 is the same as the first preferred embodiment. The light sources 111, 112 and 113 emit red light, while the light source 120 emits infrared light.

The red light emitted from the light source 111 is reflected at a selective reflection mirror 30a and is directed to the inspected area AR. On the other hand, the red lights emitted from the light sources 112 and 113 are directly applied to the inspected area AR.

The selective reflection mirror 30a is attached to the supporting members 116 and 117, and entirely covers the angular aperture $\omega_0$ (FIG. 15) of the imaging lens system 140. The selective reflection mirror 30a is inclined from the optical axis LA of the imaging lens system 140 by 45°.

Figure 15:
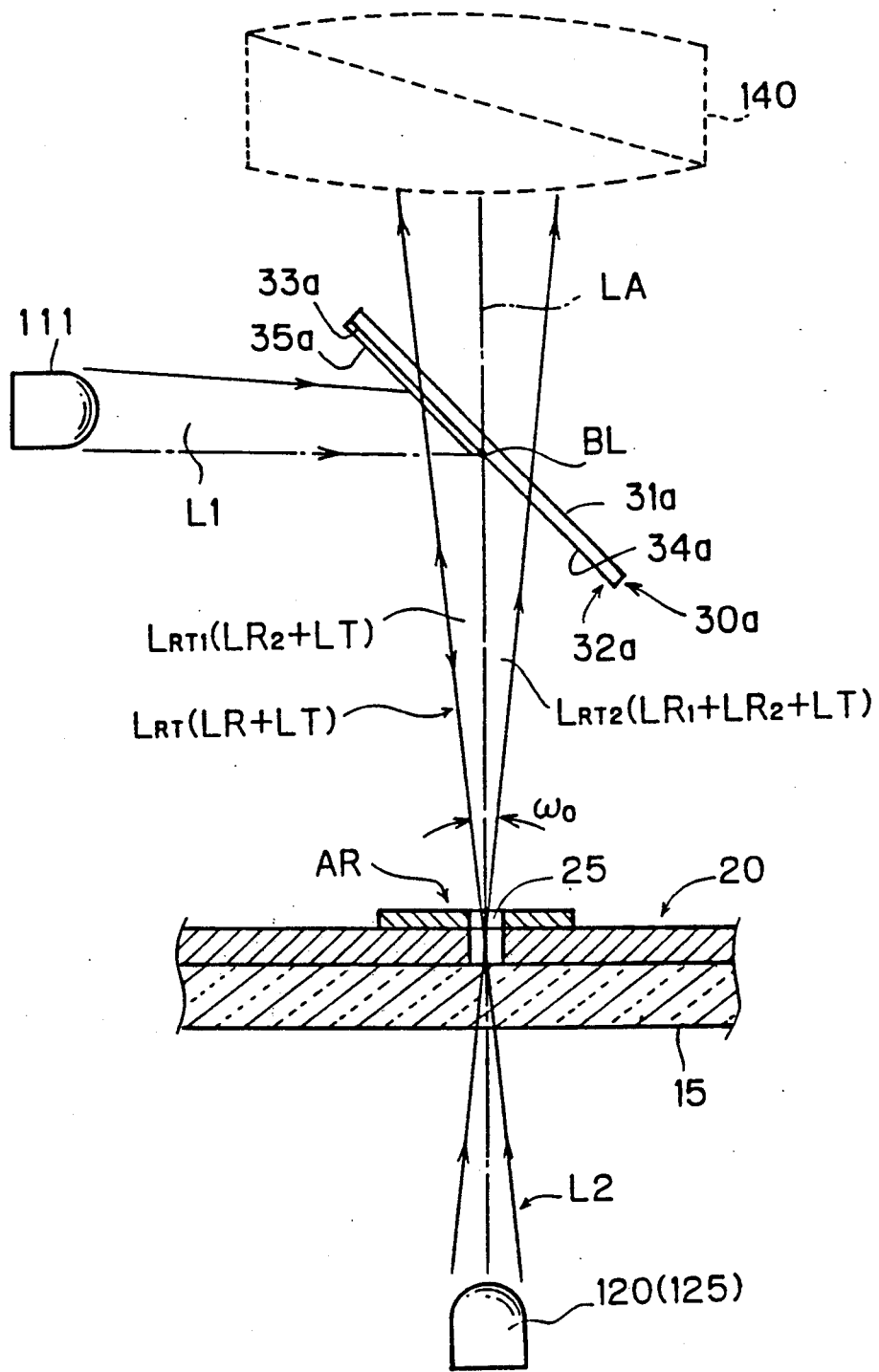
FIG. 15 is a conceptional view of the major portion of the optical head shown in FIG. 14A.

As shown in FIG. 15, the mirror 30a comprises a plane substrate 31a made of transparent glass. Preferably, the thickness of the plane substrate 31a is equal to or less than 10 mm. A major surface of the plane substrate 31a is conceptionally divided into two regions 33a and 34a, whose boundary line BL extends in the direction perpendicular to the drawing sheet. The mirror 30a is positioned so that the boundary line BL substantially crosses the optical axis LA at a right angle, i.e., 90°. The boundary line BL, therefore, substantially divides the angular aperture $\omega_0$ into two equal parts.

A thin film 35a formed of $TiO_2$, $CeO_2$, $ZnO_2$ or $SiO_2$, for example, is provided on the first region 33a. The thickness of the thin film 35a is about 650 nm (=0.65 μm).

Therefore, the first region 33a is a cold mirror region which substantially transmits light having wavelength longer than a characteristic critical wavelength but substantially reflects light having wavelength shorter than the critical wavelength. For example, when the thickness of the thin film 35a is about 650 nm, the critical wavelength thereof is about 700 nm. Thus, when the light for reflective illumination having wavelength $\lambda_1$ (=600-700 nm) is incident on the first region 33a, the light is reflected at the first region 33a. On the other hand, when the light for transmitting illumination having wavelength $\lambda_2$ (=700-1000 nm) is incident on the first region 33a, the light is transmitted through the first region 33a.

The light source 111 for regular reflection faces the fist region 33a, and the red light $L_1$ (FIG. 7) emitted from the light source 111 is reflected on the first regoin 33a to be directed to the inspected area AR of a printed circuit board 20. As already described with reference to FIGS. 14A and 14B, the red lights from the light sources 112 and 113 for irregular reflection are directly applied to the inspected area AR. These red lights are reflected on the inspected area AR to become reflected light LR containing image information of the wiring pattern. The infrared light emitted from the light source 120 for transmitting illumination is incident on the back surface of the printed circuit board 20, and a part thereof entering the through hole 25 passes through the through hole 25 to become transmitted light containing image information of the through hole 25. These reflected light and the transmitted light are spatially overlapped to become compound light $L_{RT}$, which is incident on the mirror 30a.

The reflected light incident on the angular aperture or the entrance pupil of the imaging lens system 140 includes regular reflection light $LR_1$ and irregular reflection light $LR_2$. The regular reflection light $LR_1$ is obtained through regular reflection of the light from the light source 111 on the inspected region AR, while irregular reflection light $LR_2$ is obtained through irregular reflection of the lights from the light sources 112 and 113 on the inspected region AR. In positional arrangement of the compound light $L_{RT}$ travelling from the inspected area AR to the angular aperture of the imaging lens system 140, the compound light $L_{RT}$ consists of a first portion $L_{RT1}$ incident on the first region 33a of the mirror 30a and a second portion $L_{RT2}$ incident on the second region 34a. The irregular reflection light $LR_2$ is included in both of the first portion $L_{RT1}$ and the second portion $L_{RT2}$, while the regular reflection light $LR_1$ is included only in the second region $L_{RT2}$. This is because the light from the light source 111 for regular reflection is reflected only on the first region 33a of the mirror 30a is detected to the inspected area AR, and therefore, the light from the light source 111 is incident on the inspected area AR from the left side of the optical axis LA in FIG. 15, so that the regular reflection light is obtained only in the right side of the optical axis LA. The transmitted light LT from the light source 120 is included both of the first portion $L_{RT1}$ and the second portion $L_{RT2}$.

The transmitted light LT included in the compound light $L_{RT}$ is transmitted through the mirror 30a to enter the upper space of the mirror 30a regardless of whether the same is incident on the first region 33a or the second region 34a.

The regular reflected light $LR_1$ is transmitted through the second region 34a and enters the upper space of the mirror 30a.

With respect to the irregular reflection light $LR_2$, a part incident on the first region 33a is reflected on the region 33a and propagation thereof to the upper space of the mirror 30a is prevented, while another part incident on the second region 24a is transmitted through the region 34a and enters the upper space of the mirror 30a.

Therefore, within the compound light $L_c$ incident on the imaging lens system 140, a portion $L_f$ passing through the right side of the optical axis LA in FIG. 14A includes the transmitted light LT and the reflected light LR, while another portion $L_g$ passing through the left side of the optical axis LA includes only the reflected light LR.

The compound light $L_c$ having these components are incident on a cold mirror 150 through the imaging lens system 140. The cold mirror 150 is such a mirror that only infrared light is transmitted therethrough. Therefore, as is in the first preferred embodiment, the reflected red light LR included in the compound light $L_c$ is further reflected on the cold mirror 150 and is incident on a CCD linear sensor array 161. On the other hand, the transmitted infrared light LT is transmitted through the mirror 30a and is incident on another CCD linear sensor array 162.

Photoelectric conversion of the lights incident on the linear sensor array 161 and 162 and electronic processing in image processing circuits provided in the rear stage of the sensors 161 and 162 are similar to the first preferred embodiment and description thereof is omitted here. Preferably, a telecentric lens system is employed for the imaging lens system 140, as in the first and second preferred embodiments.

C-2. Advantages of Third Preferred Embodiment

The optical head H0 shown in FIGS. 14A, 14B and 15 and the inspection device employing the same have the following characteristic advantages in addition to the generic advantages of the present invention.

(1) In this optical head H0, all the optical amount of the light transmitted through the through hole 25 is usable in image detection of the through hole 25. With respect to the regular reflection light, a half the light emitted from the light source 111 to the mirror 30a is reflected on the mirror 30a and directed to the inspected area AR. After reflection on the inspected region AR, the regular reflection light propagates and enters the image sensor 161 without substantial loss of optical amount. Consequently, half the optical amount of the light emitted from the light source 111 is usable in image detection of the wiring pattern 22.

The irregular reflection light is incident on the mirror 30a and a half the optical amount thereof is reflected on the first region 33a. However, the remaining half enters the imaging lens system 140. Thus, in the image detection through regular reflection, half the total optical amount incident into the angular aperture $\xi_0$ of the imaging lens 140 is usable in the image detection of the wiring pattern 22.

As a result, utilization efficiency of the lights from the light sources 111–113 and 120 is at a high level, and incident optical amounts on the linear image sensors 161 and 162 are large in the third preferred embodiment. The images obtained are at a high contrast and are hardly influenced by noises. Accurate image detection can be attained with the optical head H0.

Figure 16:
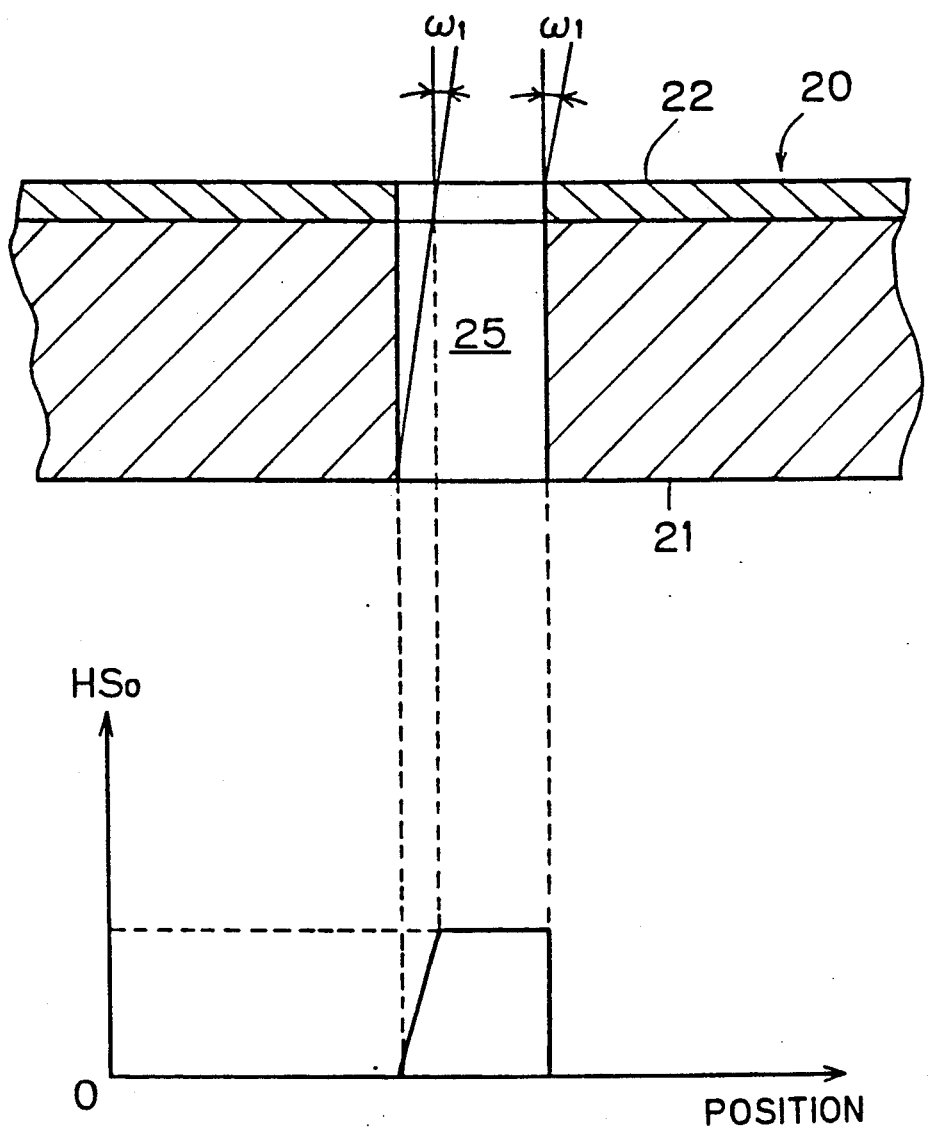
FIGS. 16 and 17 are explanatory diagrams showing relationships between angle of receiving imaging light and waveform of a hole image signal.

(2) In the first preferred embodiment shown in FIGS. 3A and 3B, the effective light flux $\xi_a$ is only half the angular aperture $\xi_0$. Thus, as shown in FIG. 16, the angle $\xi_1$ for obtaining the transmitted light through the through hole 25 is also half the angular aperture $\xi_0$ of the imaging lens system 140. Consequently, the hole image signal $HS_0$ is asymmetric around the center axis of the through hole 25, so that the accuracy in inspecting the through hole 25 is not extremely high.

Figure 17:
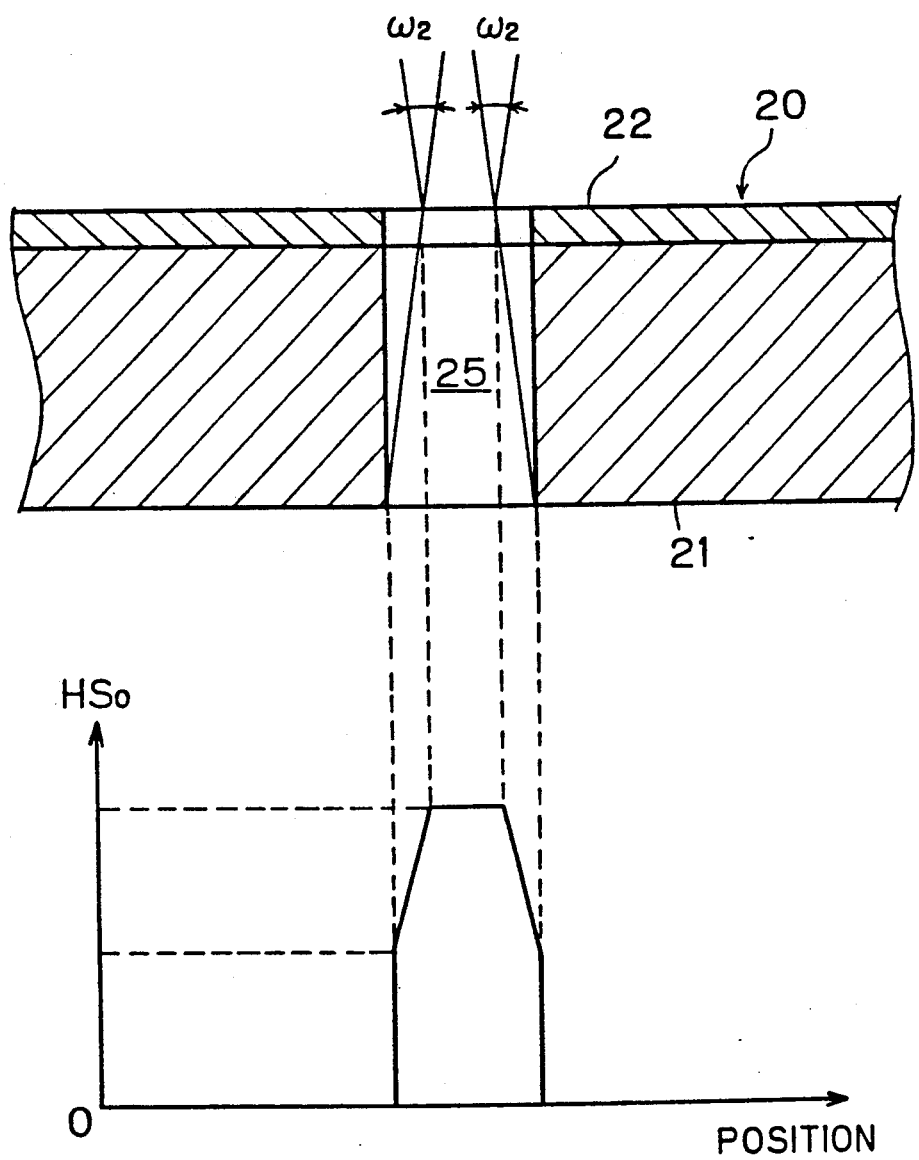

On the other hand, the third preferred embodiment is advantageous in that the angle $\xi_1$ (FIG. 17) for obtaining the transmitted light through the through hole 25 is equal to the angular aperture $\xi_0$ of the imaging lens system 140 and the hole image signal $HS_0$ is symmetric around the center axis of the through hole 25. For this reason, the accuracy in inspecting the through hole 25 is the third preferred embodiment is improved as compared with the first preferred embodiment.

D. Fourth Preferred Embodiment

Figure 18A:
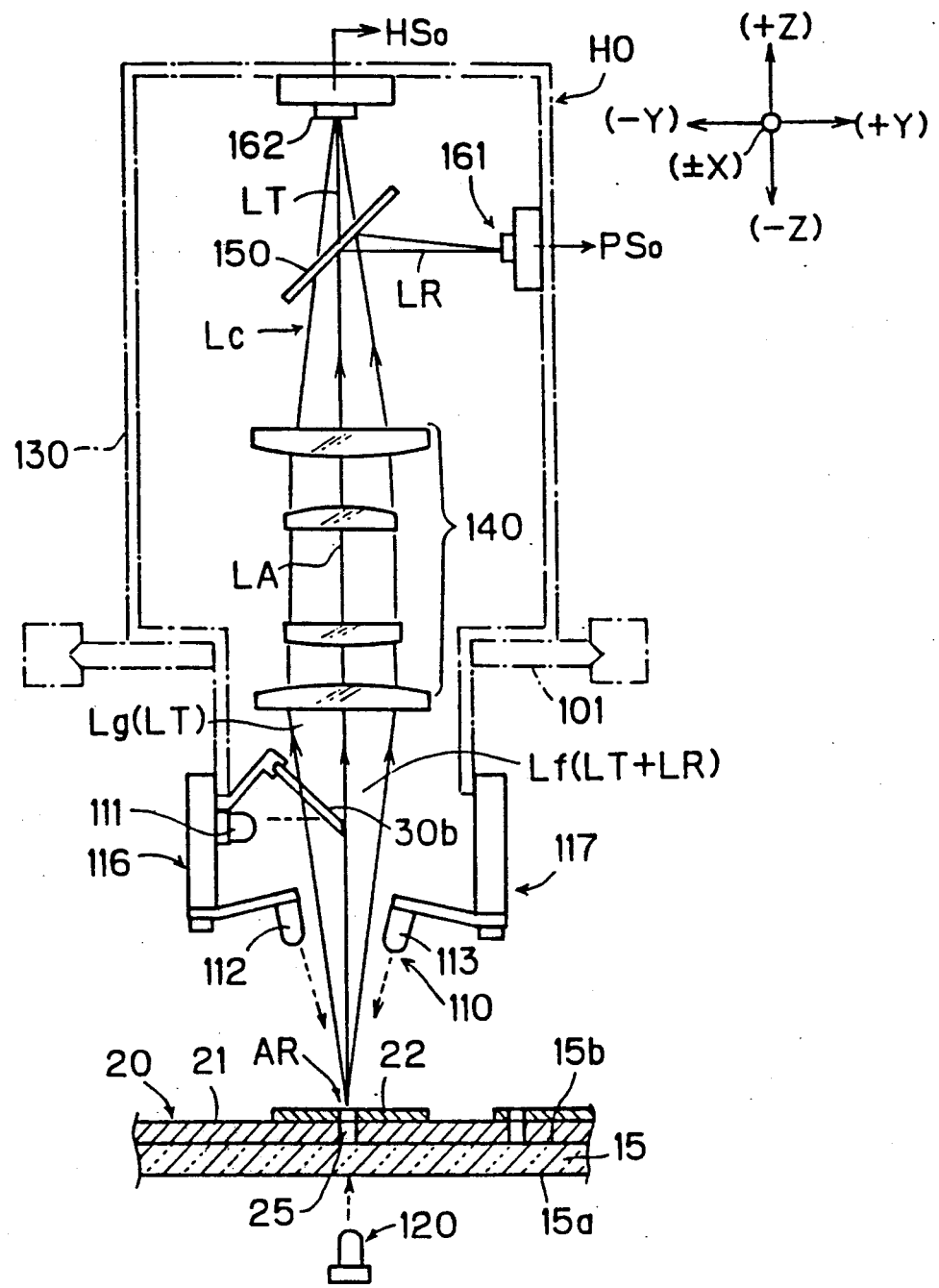
FIG. 18A is a conceptional side elevational view of an optical head according to a fourth preferred embodiment of the present invention.
Figure 18B:
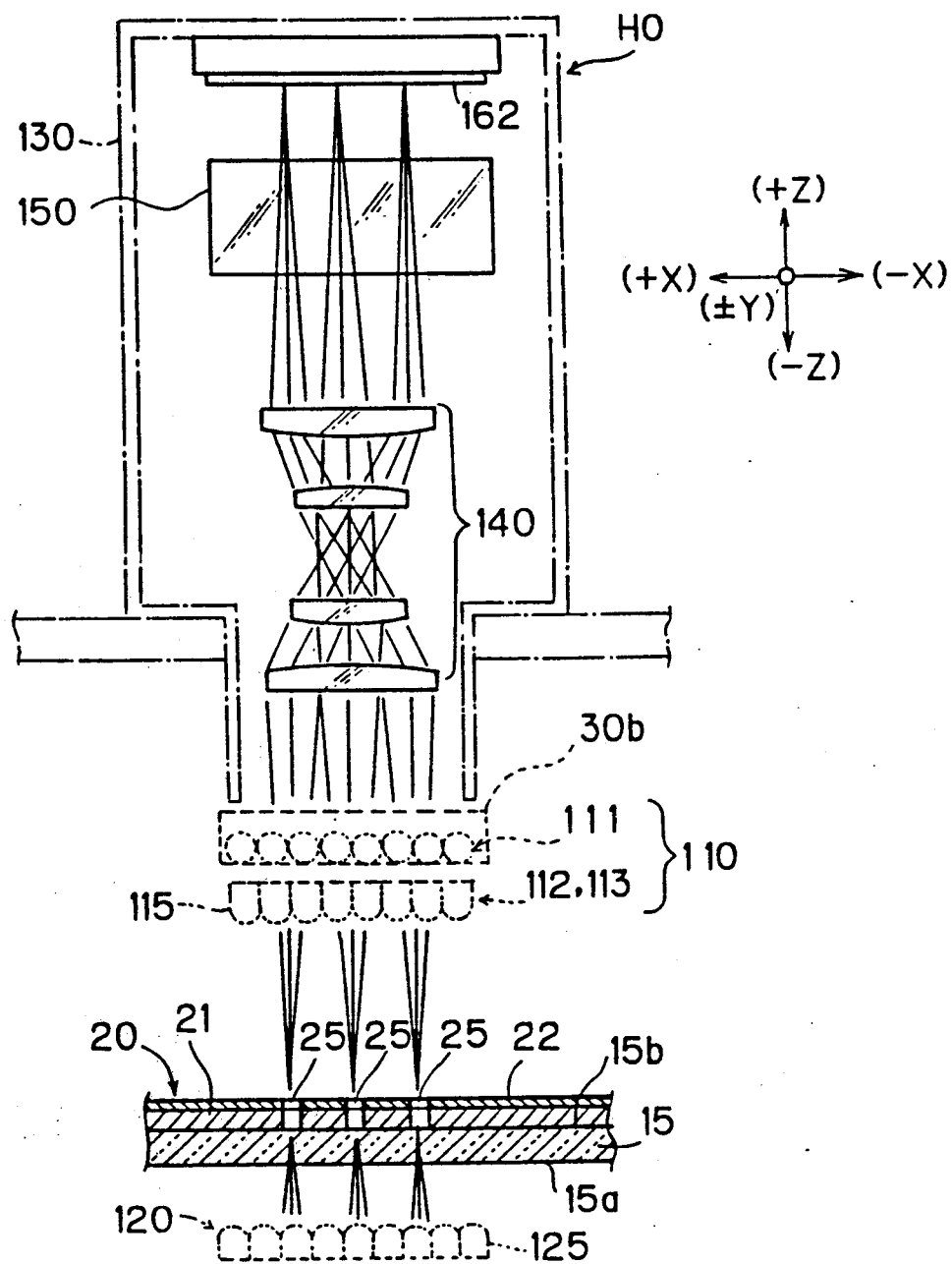
FIG. 18B is a conceptional front elevational view of the optical head shown in FIG. 18A.
Figure 19:
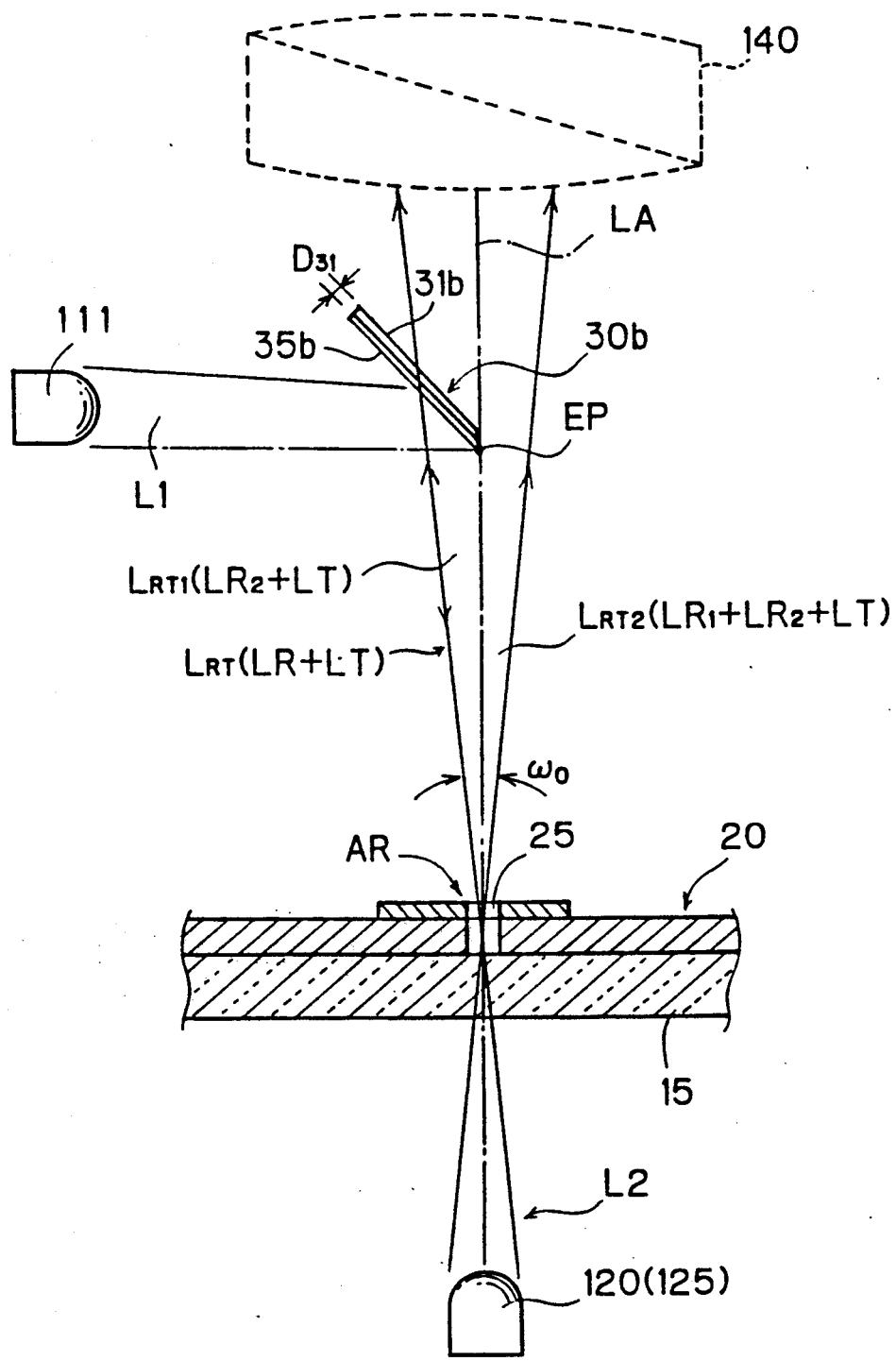
FIG. 19 is a conceptional view of the major portion of the optical head shown in FIG. 18A.

FIGS. 18A, 18B and 19 are a schematic side view, a schematic front view and a schematic view showing major portion of an optical head H0 according to a fourth preferred embodiment of the present invention, respectively. In the following description, only the difference between the third and fourth preferred embodiment is described.

The optical head H0 according to the forth preferred embodiment comprises a selective reflection mirror 30b under an imaging lens system 140. As shown in FIG. 19, the mirror 30b has a plane substrate 31b made of transparent glass, on which a thin film 35b is deposited. The thin film 35b serves as a selective light-reflection layer. Preferably, the thickness of the plane substrate 31b is 50 μm or less. The material and the thickness of a thin film 35b are the same as the thin film 35a in the third preferred embodiment. Accordingly, respective regions on the mirror 30b reflect the light for reflective illumination and transmit the light for transmitting illumination.

The mirror 30b is inclined from the optical axis LA of the imaging lens system 140 by 45° and a light source 111 for regular reflection is arranged to face the mirror 30b. An edge EP of the mirror 30b is located on the optical axis LA and the mirror 30b covers about half of the angular aperture of the imaging lens system 140.

About half the light emitted from the light source 111 for regular reflection is reflected on the mirror 30b to be applied to the inspected area AR. Respective light path of the light from the light source 112 and 113 for irregular reflection is the same as the third preferred embodiment.

Within the compound light $L_{RT}$ from the inspected area AR, a part passing through the left side of the optical axis LA enters the mirror 30b, while another part passing through the right side of the optical axis LA progresses in side space of the mirror 30b and reaches the space above the mirror 30b without entering the mirror 30b. Accordingly, the right half portion Lf (FIG. 18A) and the left half portion Lg of the compound light have the same components as the third preferred embodiment. The compound light going out of the imaging lens system 140 is divided into reflected light LR and transmitted light Lt with a dichroic mirror 150 and these lights LR and LT are detected by CCD linear image sensors 161 and 162, respectively. Respective images of the wiring pattern 22 and the through hole 25 are detected through this process and are delivered to inspection circuits. Therefore, this fourth preferred embodiment has advantages similar to the third preferred embodiment.

Figure 20:
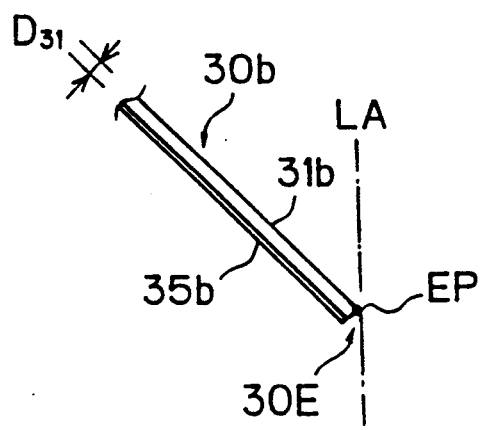
FIGS. 20 and 21 are diagrams showing the shape of the edge of selective reflection mirror.
Figure 21:
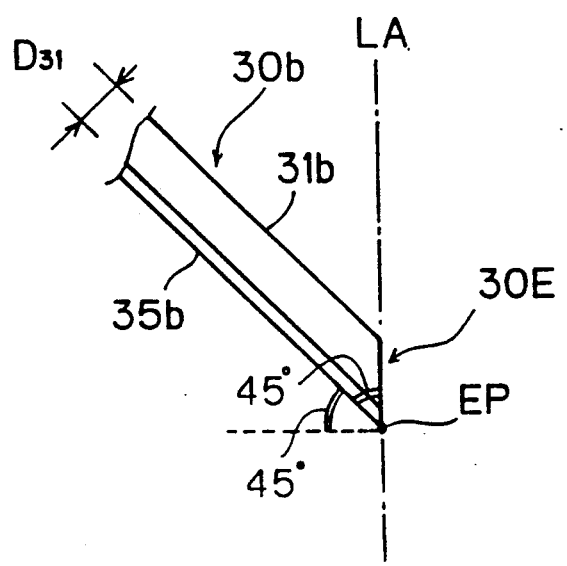

When the thickness $D_{31}$ of the plane substrate or glass plate 31b is relatively small, the edge surface 30E (FIG. 20) may be perpendicular to the photo-reflective major surface of the mirror 30b. On the other hand, when the thickness $D_{31}$ is relatively large, it is preferred that the edge surface 30E is processed to a wedge of 45° so that the edge surface 30E is in parallel to the optical axis LA. Such a modification allows all the light flux passing through the left side of the optical axis LA to another the mirror 30b without causing the condition that part of the light passing through the right side of the optical axis LA is refracted by the substrate 31b.

Figure 22:
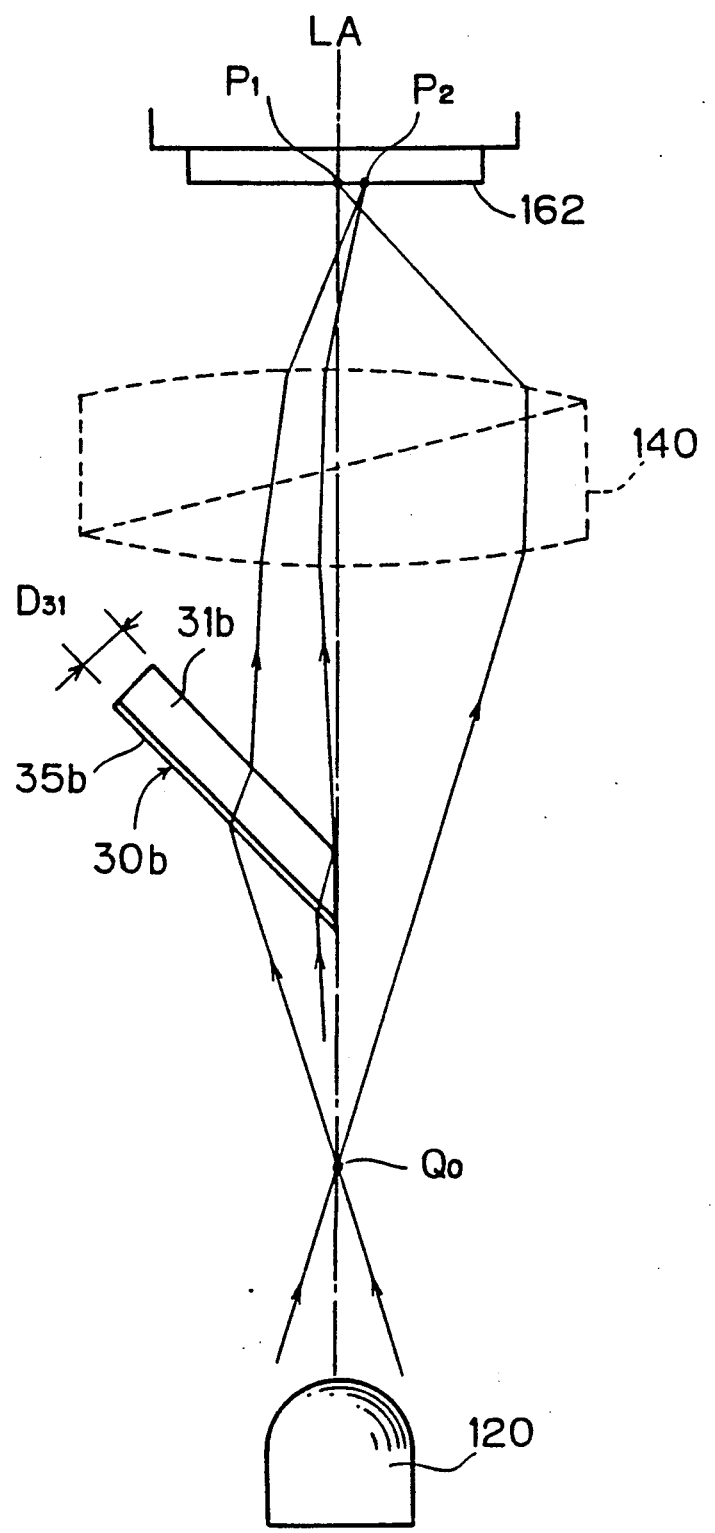
FIG. 22 is an explanatory diagram showing influence of the thickness of the mirror on imaging position.

Preferably, the thickness $D_{31}$ of the substrate 30b is made thin regardless of whether the edge surface 30E is shaped into a wedge or not. If the thickness $D_{31}$ is extremely large as shown in FIG. 22, the light path of the transmitted light passing through a point $Q_0$ is changed to a high degree due to refraction in the substrate 30b and, as a result, a convergent point $P_1$ of the light passing through the right side of the optical axis LA is largely deviated from a point $P_2$ at which the light passing through the left side of the optical axis LA. Preferably, the thickness $D_{31}$ is so determined that the distance between the points $P_1$ and $P_2$ is equal to or less than value $\Delta y$ (not shown), where the value $\Delta y$ is a predetermined allowable limit of the error in conversion of the light on the photo-electric conversion plane of the linear image 162.

E. Fifth Preferred Embodiment

Figure 23A:
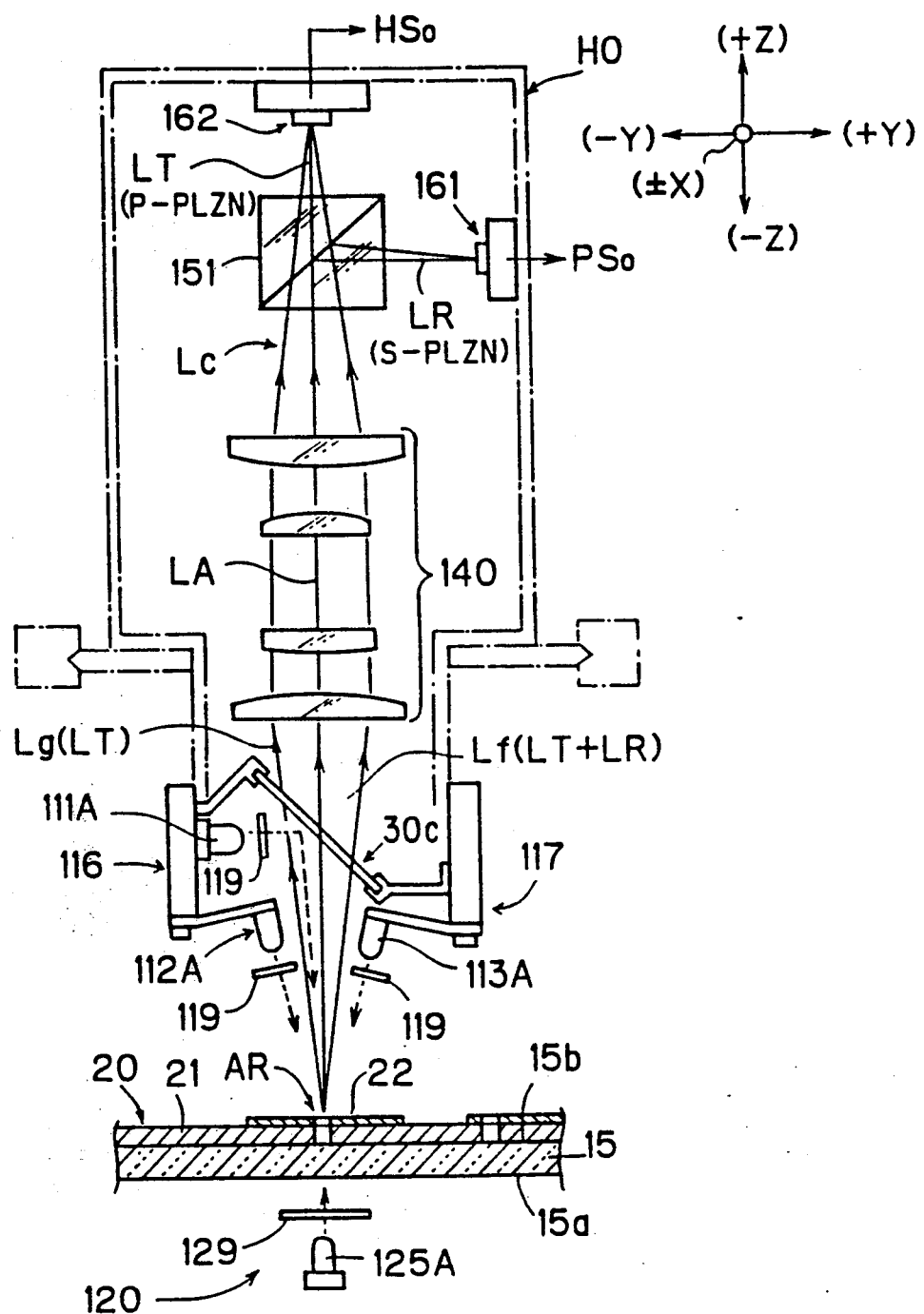
FIG. 23A is a conceptional side elevational view of an optical head employed according to a fifth preferred embodiment of the present invention.
Figure 23B:
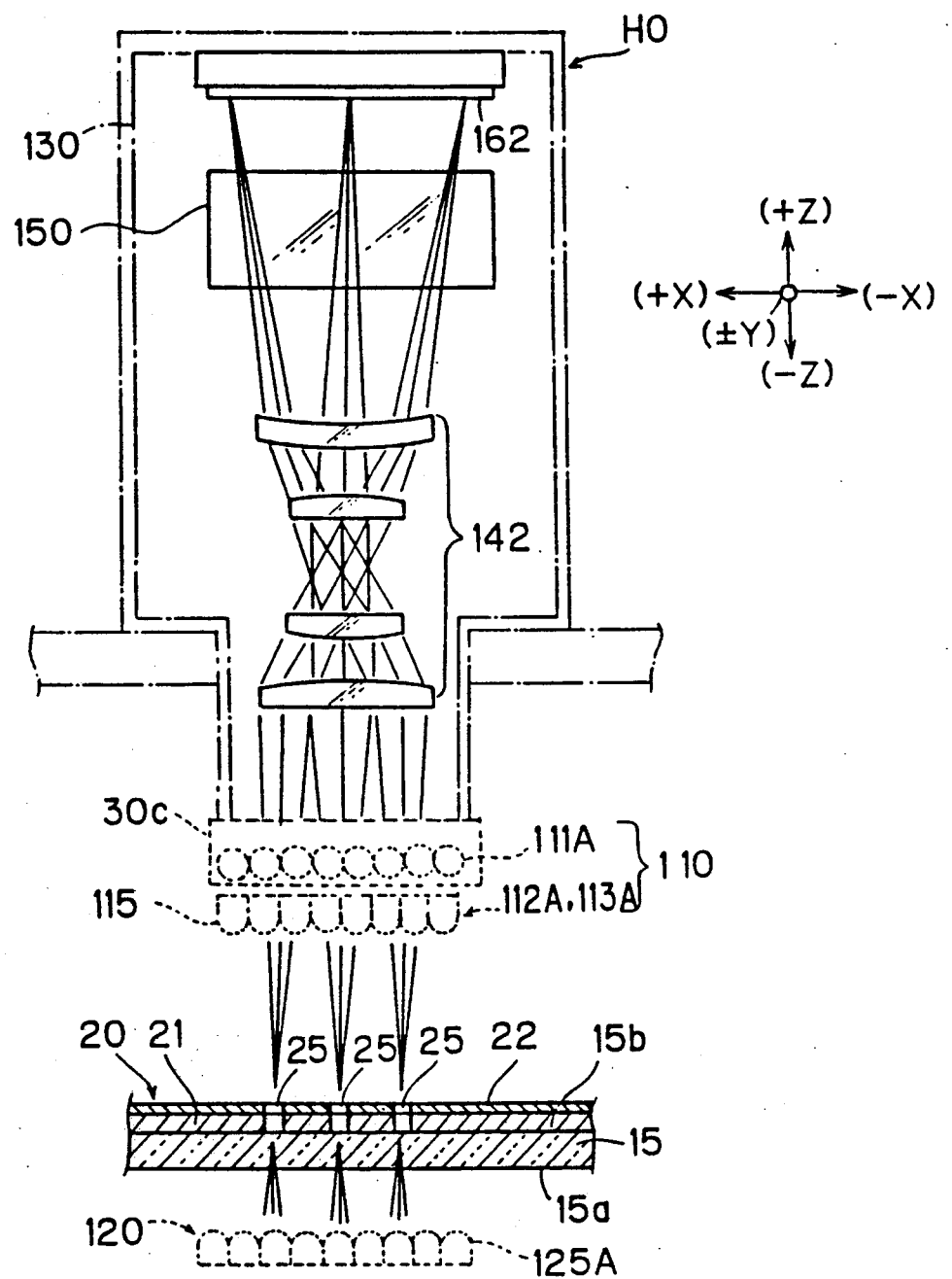
FIG. 23B is a conceptional front elevational view of the optical head shown in FIG. 23A.
Figure 24:
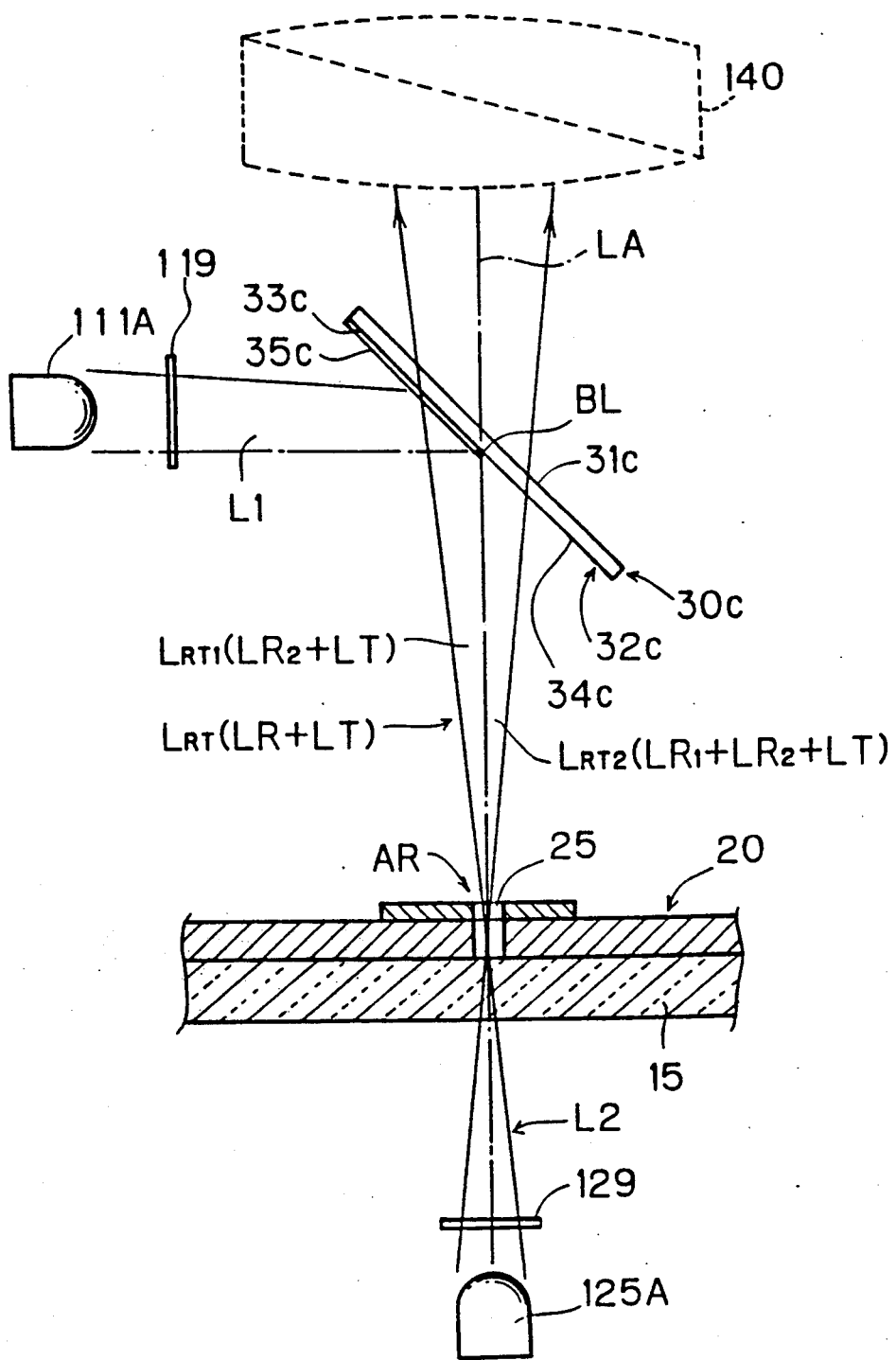
FIG. 24 is a conceptional view of the major portion of the optical head shown in FIG. 23A.

FIGS. 23A, 23B and 24 are a schematic side view, a schematic front view and a schematic view showing major portion of an optical head H0 according to a fifth preferred embodiment of the present invention, respectively.

Although the third preferred embodiment is similar to the third preferred embodiment, difference therebetween is in that light for reflective illumination and that for transmitting illumination are separated from each other through distinction between polarized lights rather than distinction of wavelength.

That is, according to the fifth preferred embodiment, a light source system for reflective illumination comprises combination of the white light sources 111A, 112B and 113B and S-wave polarizing plates 119. Accordingly, the light for reflective illumination is S-wave, i.e., light whose electric field vector is in $(\pm X)$ directions. The polarizing plates 119 are supported from the optical head H0 side through supporting members (not shown).

On the other hand, a light source system 120 for transmitting illumination consists of white light sources 125A and P-wave polarizing plate 129. The P-wave polarizing plate 129 is supported in the system 120 through supporting members (not shown). Accordingly, the light for transmitting illumination is P-wave, i.e., light whose electric vector is in XZ-plane.

A mirror 30c provided under an imaging lens system 140 converse the whole area of the angular aperture $\xi_0$ of the imaging lens system 140. The mirror 30c comprises a plane substrate 31c made of transparent glass as shown in FIG. 24, and a major surface of the plane substrate 31c is conceptionally divided into a first region 33c and a second region 34c similarly to the third preferred embodiment shown in FIGS. 14A, 14B and 15. The boundary line BL between the first region 33c and the second region 34c crosses the optical axis LA of the imaging lens system 140 at a right angle. Accordingly, the boundary line BL of the regions 33c and 34c substantially divides the angular aperture $\xi_0$ into equal two parts.

Within these regions 33c and 34c, the first region 33c is provided thereon with a thin film 35c for splitting light into respective polarized components. The thin film 35c is made of combination of $MgF_2$ and $PbF_2$, for example, and the thickness thereof is about 750 nm (=0.75 μm). Similarly to the light-slitting phenomenon in dichroic mirrors, the first region 33c transmits P-polarized light and reflects S-polarized light. Consequently, the light from the light source 111A for regular reflection is reflected on the first region 33c to be applied to the surface of a printed board 20.

The S-polarized lights from the light sources 111A, 112A and 113A are reflected on the wiring pattern 22, while the P-polarized light from the light source 120 transmitted through a through hole 25. A compound light $L_{RT}$, which is a combination the reflected light and the transmitted light, enters the mirror 30c. Optical character and function of the mirror 30c is understood by rewriting "the lights of respective wavelength" in the description of the third preferred embodiment to "the lights of respective polarizations". The imaging lens system 140 receives the compound light consisting of the S-polarized light and the P-polarized light.

The compound light enters a polarized beam splitter 151. The polarized beam splitter 151 transmits S-wave and reflects P-wave. Consequently, the S-polarized reflected light LR (FIG. 23A) having image information of the wring pattern 22 is imaged on the photo-electric conversion plane of a linear image sensor 161, while the P-polarized reflected light LT having image information of the through hole 25 is imaged on the photoelectric conversion plane of another linear image sensor 162. The other construction is the same with the third preferred embodiment.

Since respective images of the wiring pattern 22 and the through hole 25 are independently and simultaneously detected by the different image sensors 161 and 162, the fifth preferred embodiment has advantages similar to the third and fourth preferred embodiments, which advantages includes improvement in utilization efficiency of photoamount of lights.

In one modification, the light for reflective illumination may be P-polarized light, while the light for transmitting illumination may be S-polarized light. when light sources emitting polarized lights, such as laser, are employed, polarizing plates 119 and 129 may be omitted.

F. Sixth Preferred Embodiment

Figure 25A:
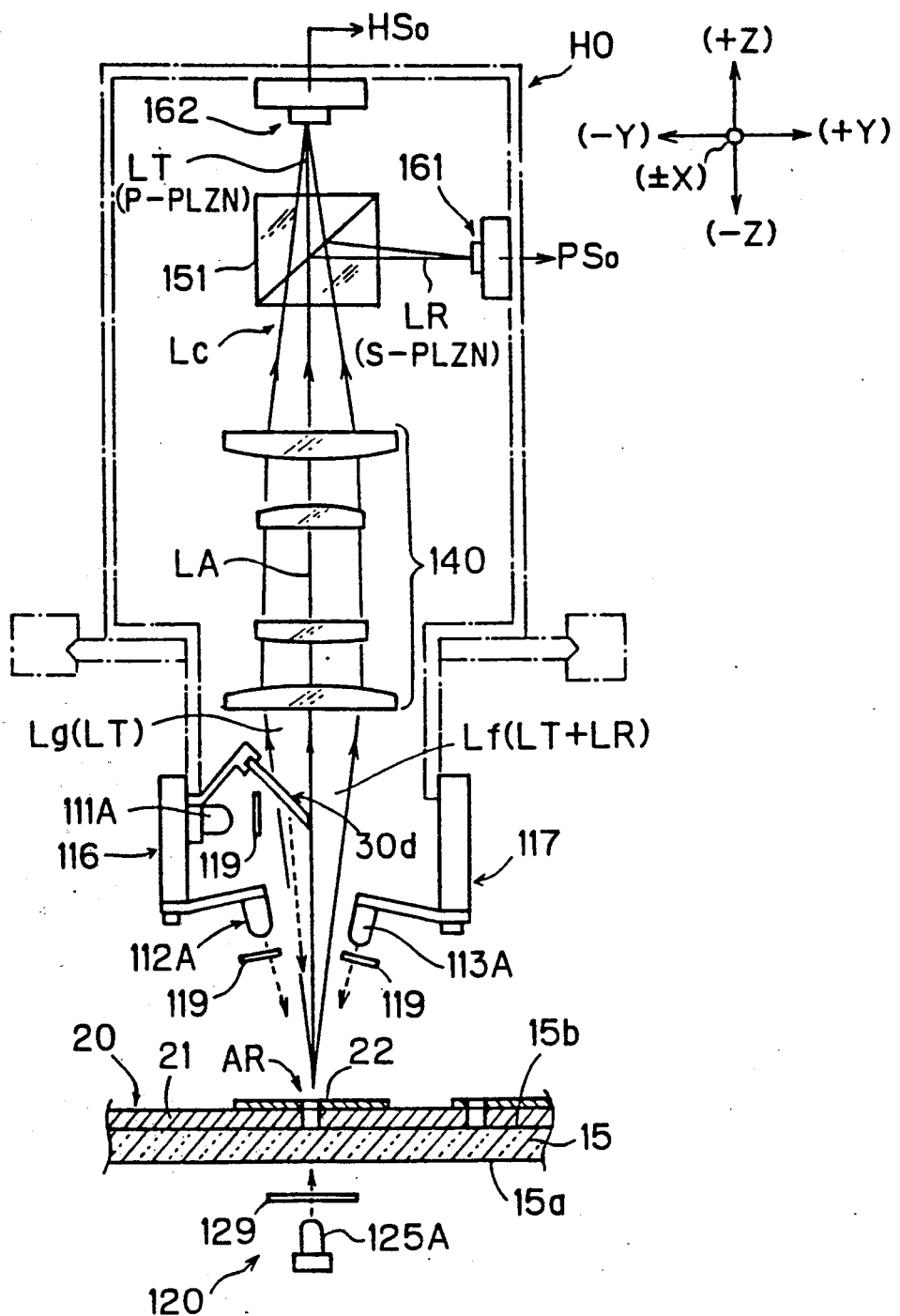
FIG. 25A is a conceptional side elevational view of an optical head according to a sixth preferred embodiment of the present invention.
Figure 25B:
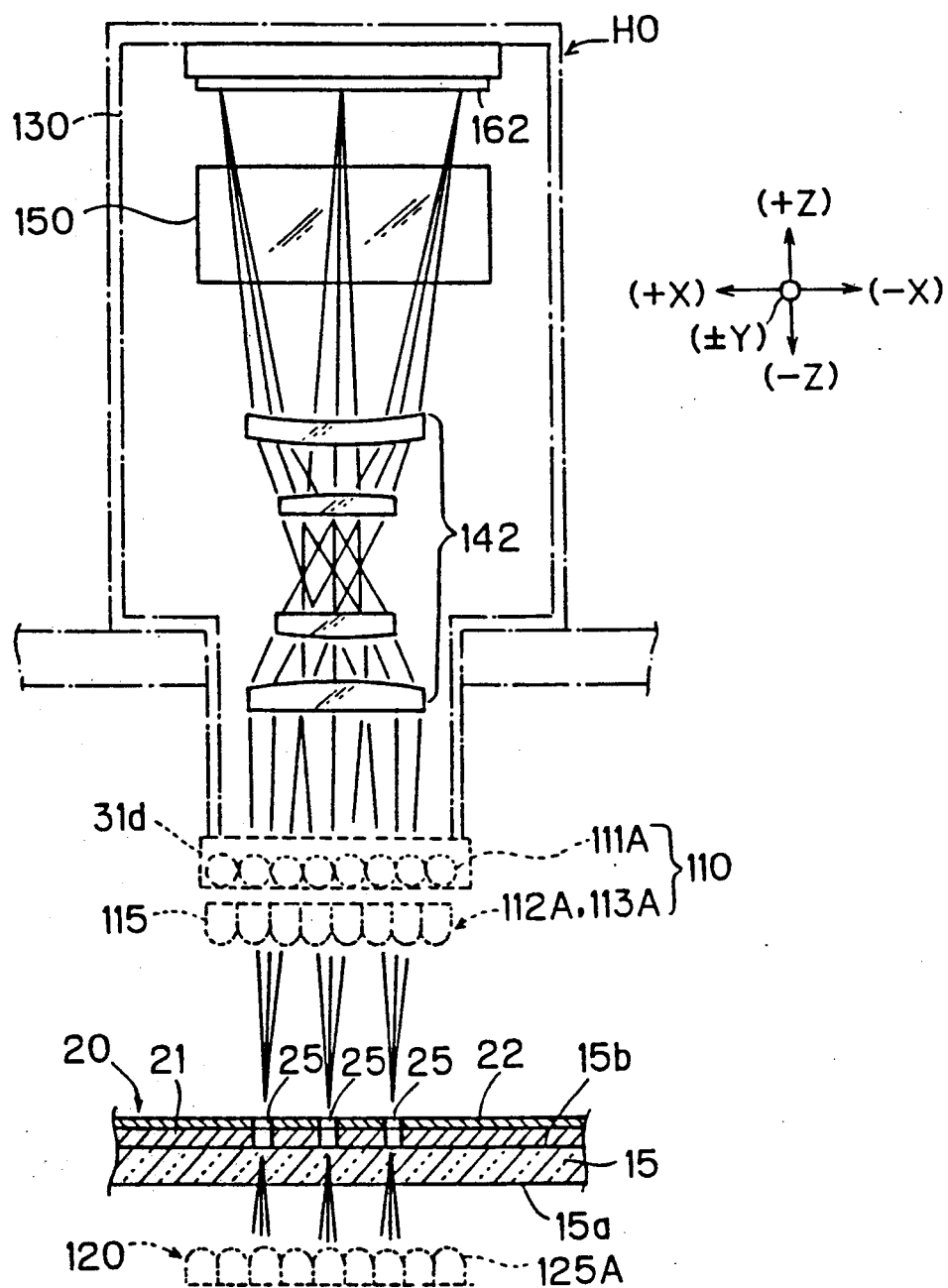
FIG. 25B is a conceptional front elevational view of the optical head shown in FIG. 25A.
Figure 26:
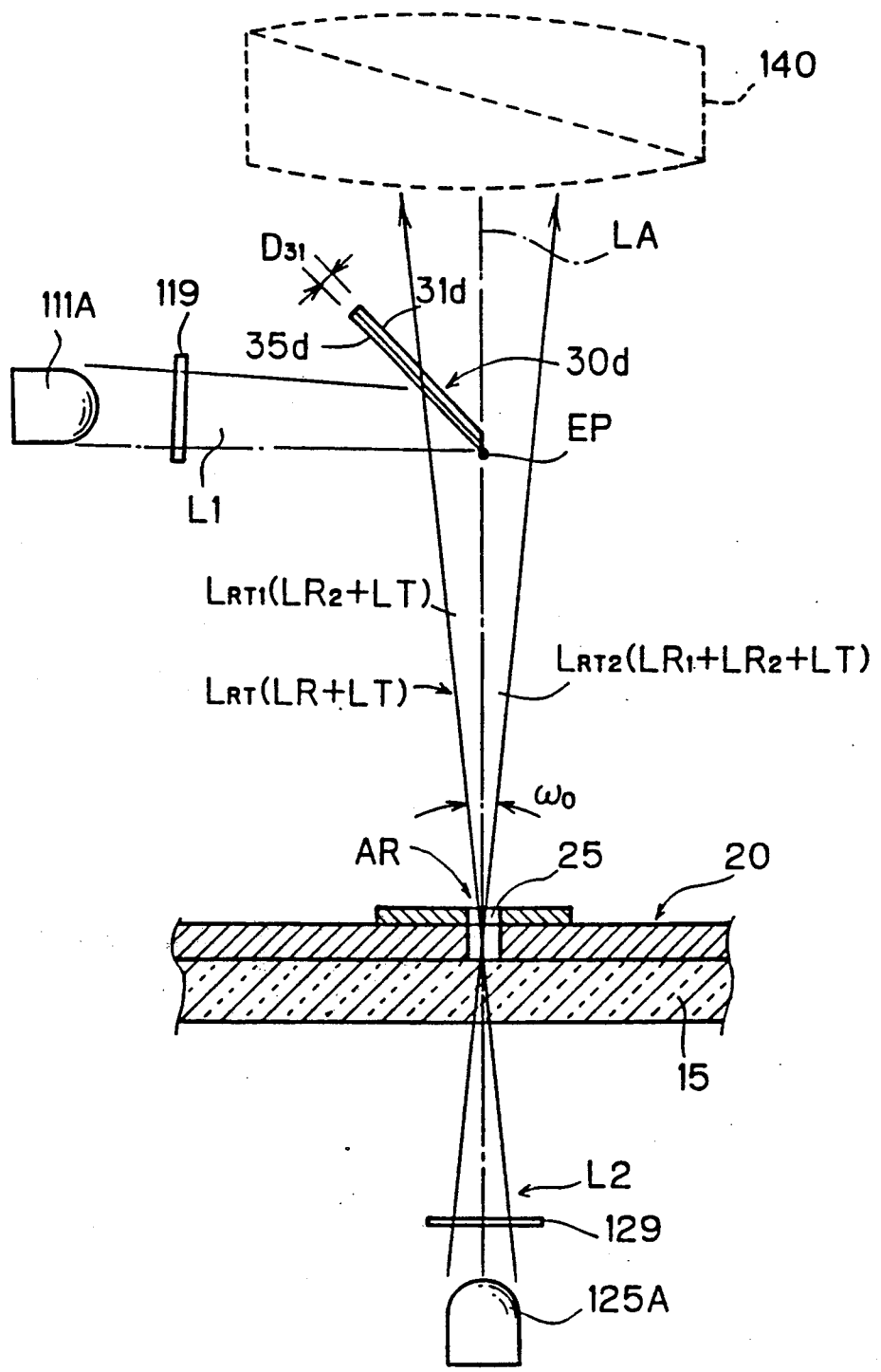
FIG. 26 is a conceptional view of the major portion of the optical head shown in FIG. 25A.
Figure 28:
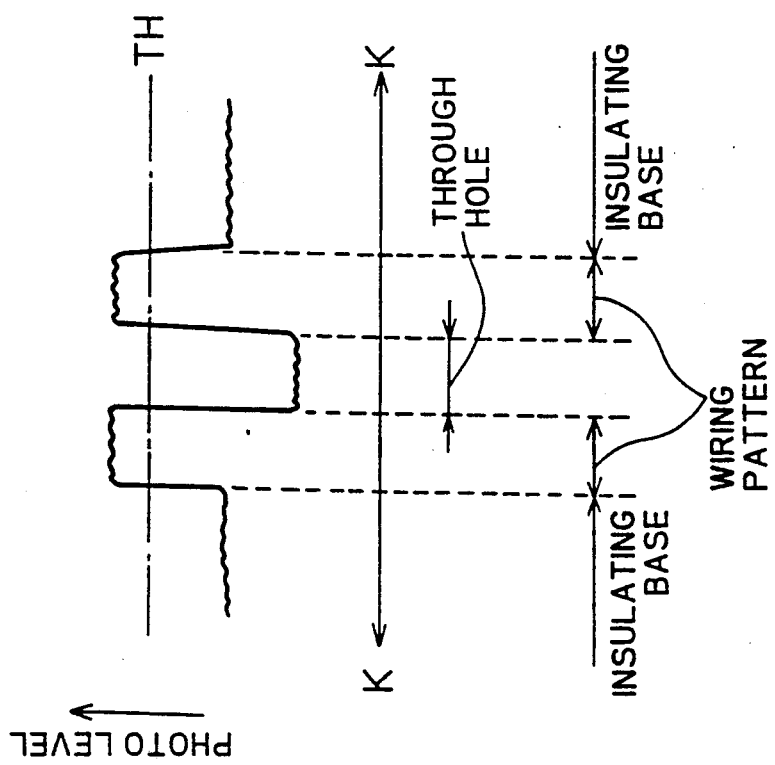
FIG. 28 is a waveform diagram showing exemplary image signals obtained by the system of FIG. 27.

A sixth preferred embodiment is shown in FIGS. 25A, 25B and 26. An optical head H0 according to the sixth preferred embodiment is a combination of the fourth and fifth preferred embodiments. That is, two kinds of lights are splitted through the technique of polarized light splitting, while the optical head H0 is provided with a mirror 30d having the same shape and located at the same position as the mirror 30b in FIG. 19. The mirror 30d comprises a transparent glass substrate on which a thin film 35d for polarization splitting is formed. An edge EP of the mirror 30d crosses the optical axis LA of an imaging lens system at a right angle. The operation of this sixth preferred embodiment will be understood by those skilled in the art from the description of the fourth and fifth preferred embodiments, and therefore, the description of the operation of the sixth preferred embodiment is omitted here.

G. Modifications and Conclusion (1) In the third and fourth preferred embodiments, lights having different wavelength may be employed as light for reflective illumination and that for transmitting illumination, and they are not limited to red light and infrared light. When visible lights having different wavelength are employed, the cold mirror 150 is replaced with a dichroic mirror. Each of the light sources 110 and 120 may be composed of a white light source and a color filter.

(2) In the third and fifth preferred embodiments, utilization efficiency of lights takes a maximum value, when the boundary line BL of the first and second regions crosses the optical axis. However, the boundary line BL may be deviated from the optical axis LA. Further, in the fourth and sixth preferred embodiments, the edge EP of the edge of the mirror 30$b$ or 30 $d$ may be deviated from the optical axis LA. Although it is preferred that the mirror 30$b$ or 30$d$ is located so as to cover half the angular aperture $\omega_0$ of the imaging lens system, the present invention is effective as long as the mirror 30$b$ or 30$d$ may cover a part of the angular aperture $\omega_0$.

While the invention has been shown and described in detail, the foregoing description is in all aspects illustrative and not restrictive. It is therefore understood that numerous modifications and variations can be devised without departing from the scope of the invention.

We claim:

1. A method of reading an image of an object with an imaging optical system having a respective angular aperture associated therewith and with an image sensor, comprising the steps of:
   (a) providing a light source at a position located within only a portion of said angular aperture of said imaging optical system;
   (b) locating said object in a visual field of said imaging optical system;
   (c) applying illumination light from said light source to said object, wherein said illumination light reflects on said object to obtain a reflected light; and
   (d) receiving said reflected light by said image sensor through said imaging optical system to thereby obtain an image of said object.

2. The method of claim 1, wherein
said step (a) comprises the step of:
   (a-1) positioning an edge of said light source on an optical axis of said imaging optical system.

3. The method of claim 2, wherein
said step (a) further comprises the step of:
   (a-2) covering half said angular aperture of said imaging optical system with said light source.

4. An image reading system for reading an image of an object, comprising:
   (a) an imaging optical system having a respective angular aperture and facing said object;
   (b) light source means located within only a portion of said angular aperture of said imaging optical system and effective for emitting illumination light toward said object, wherein said illumination light is reflected on said object to become a reflected light; and
   (c) image sensor means provided in the opposite side of said object across said imaging optical system, for receiving said reflected light through said imaging optical system to obtain an image of said object.

5. The image reading system of claim 4, wherein said light source means has an edge located on an optical axis of said imaging optical system.

6. The image reading system of claim 5, wherein
said light source means has a body covering half said angular aperture of said imaging optical system.

7. The image reading system of claim 6, wherein
said light source means is a first light source means;
said illumination light is a first illumination light;
said reflected light is a first reflected light; and
said image reading system further comprises:
   (d) a second light source means provided out of said angular aperture, for emitting a second illumination light toward said object, wherein said second illumination light is reflected on said object to become a second reflected light, said second reflected light being received by said image sensor.

8. The image reading system of claim 7, which is provided for inspecting a printed board having an insulating substrate on which a wiring pattern is formed and through which a through hole is provided: wherein
said printed board is said object;
said imaging optical system is located to face said wiring pattern;
said first and second light source means are located between said printed board and said imaging optical system for applying said first and second illumination lights for illuminating said wiring pattern.

9. The image reading system of claim 8, wherein
said image sensor means is a first image sensor; and
said image reading system further comprises:
   (e) a third light source means provided in the opposite side of said imaging optical system across said printed board, for emitting a third illumination light to said through hole, wherein said third illumination light is transmitted through said through hole to become a transmitted light which then meets said first and second reflected lights and passes through said imaging optical system in the form of a compound light consisting of said first and second reflected lights and said transmitted light;
   (f) a second image sensor provided in a different position from said first image sensor; and
   (g) light splitting means provided in the opposite side of said printed board across said imaging optical system, for splitting said compound light into:
said first and second reflected lights and;
said transmitted light, and for directing:
said first and second reflected lights to said first image sensor; and
said transmitted light to said second image sensor.

10. The image reading system of claim 9, wherein
said first and second illumination lights have a first wavelength;
said third illumination light has a second wavelength; and
said light splitting means comprises;
   (g-1) optical means for splitting said compound light into said first and second reflected lights and said transmitted light according to respective wavelength thereof.

11. The image reading system of claim 9, wherein
said first and second illumination lights are polarized in a first direction;
said third illumination light is polarized in a second direction; and
said light splitting means comprises;

(g-2) optical means for splitting said compound light into said first and second reflected lights and said transmitted light according to respective directions.

12. The image reading system of claim 9, wherein said imaging optical system is telecentric in at least a side of said printed board.

13. A method of reading respective images of a wiring pattern and a through hole of an printed board having first and second surfaces opposite to each other, in which said wiring pattern is formed on said first surface and said through hole is provided between said first and second surfaces, said method comprising the steps of:
   (a) applying a first light having a first wavelength to said first surface of said printed board, wherein said first light is reflected on said wiring pattern to become a reflected light;
   (b) applying a second light having a second wavelength to said second surface of said printed board, wherein said second light is transmitted through said through hole to become a transmitted light;
   (c) obtaining a compound light consisting of said reflected light and said transmitted light;
   (d) leading said compound light to an imaging optical system;
   (e) receiving with a light splitter said compound light which has passed through said imaging optical system to split said compound light into said reflected light and said transmitted light;
   (f) receiving said reflected light with a first image sensor to obtain an image of said wiring pattern; and
   (g) receiving said transmitted light with a second image sensor to obtain an image of said through hole;
wherein said step (a) comprises the steps of:
   (a-1) applying a first component of said first light from a position located within only a portion of an angular aperture of said imaging optical system to said first surface of said printed board; and
   (a-2) applying a second component of said first light from a position outside said angular aperture of said imaging optical system to said first surface of said printed board.

14. The method of claim 13, wherein said step (a-1) comprises the steps of:
providing a light source having a body whose edge is on an optical axis of said imaging optical axis; and
enabling said light source to emit said first component of said first light.

15. The method of claim 14, wherein
said first light is red light and said second light is infrared light; and
said light splitter is a cold mirror reflecting said red light and transmitting said infrared light.

16. An image reading system for reading respective images of a wiring pattern and a through hole of an printed board having first and second surfaces opposite to each other, in which said wiring pattern is formed on said first surface and said through hole is provided between said first and second surfaces, said image reading system comprising:
   (a) an imaging optical system facing said first surface of said printed board;
   (b) first light source means facing said first surface of said printed board to emit a first light having a first wavelength to said first surface of said printed board, wherein said first light is reflected on said wiring pattern to become a reflected light;
   (c) second light source means facing said second surface of said printed board to emit a second light having a second wavelength to said second surface of said printed board, wherein said second light is transmitted through said through hole to become a transmitted light which is overlapped with said reflected light to obtain a compound light entering said imaging optical system;
   (d) light splitter means for receiving said compound light which has passed through said imaging optical system to split said compound light into said reflected light and said transmitted light;
   (e) first image sensor means for receiving said reflected light to obtain an image of said wiring pattern; and
   (f) second image sensor means for receiving said transmitted light to obtain an image of said through hole;
wherein said first light source means comprises:
   (b-1) first illumination means provided in a position located within only a portion of an angular aperture of said imaging optical system to emit a first component of said first light; and
   (b-2) second illumination means located outside said angular aperture of said imaging optical system to emit a second component of said first light.

17. The image reading system of claim 16, wherein said first illumination means has a body whose edge is located on an optical axis of said imaging optical system.

18. The image reading system of claim 17, wherein said body of said first illumination means covers half said angular aperture of said imaging optical system.

19. A method of reading respective images of a wiring pattern and a through hole of an printed board having wiring and second surfaces opposite to each other, in which said wiring pattern is formed on said first surface and said through hole is provided between said first and second surfaces, said method comprising the steps of:
   (a) applying a first light polarized in a first direction to said first surface of said printed board, wherein said first light is reflected on said wiring pattern to become a reflected light;
   (b) applying a second light polarized in a second direction to said second surface of said printed board, wherein said second light is transmitted through said through hole to become a transmitted light;
   (c) obtaining a compound light consisting of said reflected light and said transmitted light;
   (d) leading said compound light to an imaging optical system;
   (e) receiving with a light splitter said compound light which has passed through said imaging optical system to split said compound light into said reflected light and said transmitted light;
   (f) receiving said reflected light with a first image sensor to obtain an image of said wiring pattern; and
   (g) receiving said transmitted light with a second image sensor to obtain an image of said through hole;
wherein said step (a) comprises the steps of:

(b-1) applying a first component of said first light from a position located within only a portion of an angular aperture of said imaging optical system to said first surface of said printed board; and (b-2) applying a second component of said first light from a position outside said angular aperture of said imaging optical system to said first surface of said printed board.

20. The method of claim 19, wherein
said step (a-1) comprises the steps of:
providing a light source having a body whose edge is on an optical axis of said imaging optical axis; and
enabling said light source to emit said first component of said first light.

21. An image reading system for reading respective images of a wiring pattern and a through hole of a printed board having first and second surfaces opposite to each other, in which said wiring pattern is formed on said first surface and said through hole is provided between said first and second surfaces, said image reading system comprising:
(a) an imaging optical system facing said first surface of said printed board;
(b) first light source means facing said first surface of said printed board to emit a first light polarized in a first direction to said first surface of said printed board, wherein said first light is reflected on said wiring pattern to become a reflected light;
(c) second light source means facing said second surface of said printed board to emit a second light polarized in a second direction to said second surface of said printed board, wherein said second light is transmitted through said through hole to become a transmitted light which is overlapped with said reflected light to obtain a compound light entering said imaging optical system;
(d) light splitter means for receiving said compound light which has passed through said imaging optical system to split said compound light into said reflected light and said transmitted light;
(e) first image sensor means for receiving said reflected light to obtain an image of said wiring pattern; and
(f) second image sensor means for receiving said transmitted light to obtain an image of said through hole;
wherein said first light source means comprises:
(b-1) first illumination means provided in a position located within only a portion of an angular aperture of said imaging optical system to emit a first component of said first light; and
(b-2) second illumination means located outside said angular aperture of said imaging optical system to emit a second component of said first light.

22. The image reading system of claim 21, wherein
said first illumination means has a body whose edge is located on an optical axis of said imaging optical system.

23. The image reading system of claim 22, wherein said body of said first illumination means covers half said angular aperture of said imaging optical system.

24. A method of reading respective images of a wiring pattern and a through hole of an printed board having first and second surfaces opposite to each other, in which said wiring pattern is formed on said first surface and said through hole is provided between said first and second surfaces, said method comprising the steps of:
(a) providing an imaging optical system;
(b) providing a selective reflection mirror covering the entirety of an angular aperture of said imaging optical system, wherein
said selective reflecting mirror having a surface which consists of:
a first region capable of reflecting a first light of a first optical character and capable of transmitting a second light of a second optical character; and
a second region capable of reflecting said first and second lights; and
said angular aperture of said imaging optical system is divided into two part with a boundary of said first and second regions;
(b) applying said first light from out of an angular aperture of said imaging optical system to said selective reflection mirror to direct said first light to said first surface of said printed board, thereby obtaining a reflected light through reflection of said first light on said wiring pattern;
(c) applying said second light to said second surface of said printed board, thereby obtaining a transmitted light through transmittance of said second light through said through hole;
(d) obtaining a compound light consisting of said reflected light and said transmitted light;
(e) leading said compound light to said imaging optical system through said selective reflection mirror,
(f) receiving with a light splitter said compound light having passed through said imaging optical system to split said compound light into said reflected light and said transmitted light;
(g) receiving said reflected light with a first image sensor to obtain an image of said wiring pattern; and
(h) receiving said transmitted light with a second image sensor to obtain an image of said through hole.

25. The method of claim 24, wherein
said first light is a light having a first wavelength;
said second light is a light having a second wavelength; and
said light splitter is a mirror reflecting only one of said first light and said second light in said compound light.

26. The method of claim 25, wherein
said first light is a light polarized in a first direction;
said second light is a light polarized in a second direction; and
said light splitter is a polarization beam splitter mirror reflecting only one of said first light and said second light in said compound light.

27. The method of claim 24, wherein
said boundary substantially divides said angular aperture into two equal parts.

28. The method of claim 27, wherein
said selective reflection mirror comprises a transparent substrate and a selective photo-reflection film selectively formed on said transparent substrate;
said first region is an exposed surface of said selective photo-reflection film; and
said second region is an exposed surface of said transparent substrate.

29. An image reading system for reading respective images of a wiring pattern and a through hole of an printed board having first and second surfaces opposite to each other, in which said wiring pattern is formed on said first surface and said through hole is provided between said first and second surfaces, said image reading system comprising:

(a) an imaging optical system;
(b) a selective reflection mirror covering whole of an angular aperture of said imaging optical system and comprising a surface which consists of:
a first region capable of reflecting a first light of a first optical character and capable of transmitting a second light of a second optical character; and
a second region capable of reflecting said first and second lights;
wherein said angular aperture of said imaging optical system is divided into two part with a boundary of said first and second regions;
(c) first light source means provided out of an angular aperture of said imaging optical system, for emitting said first light toward said selective reflection mirror to direct said first light to said first surface of said printed board to obtain a reflected light through reflection of said first light on said wiring pattern;
(d) second light source means provided in the said second surface side, for emitting said second light toward said second surface of said printed board to obtain a transmitted light through transmittance of said second light through said through hole;
wherein said reflected light and said transmitted light are overlapped with each other to form a compound light; and
said compound light enters said selective reflection mirror and then passes through said imaging optical system;
(e) light splitter means for receiving said compound light having passed through said imaging optical system to split said compound light into said reflected light and said transmitted light;
(f) first image sensor means for receiving said reflected light to obtain an image of said wiring pattern; and
(g) second image sensor means for receiving said transmitted light to obtain an image of said through hole.

30. The image reading system of claim 29, wherein said first light source means comprises:
(c-1) a first illuminator means for emitting light having a first wavelength as said first light;
said second light source means comprises:
(b-1) a second illuminator means for emitting light having a second wavelength as said second light; and
said light splitter means comprises:
(e-1) a mirror reflecting only one of said first light and said second light in said compound light.

31. The image reading system of claim 29, wherein said first light source means comprises:
(c-2) a first illuminator means for emitting light polarized in a first direction as said first light;
said second light source means comprises:
(b-2) a second illuminator means for emitting light polarized in a second direction as said second light; and
said light splitter means comprises:
(e-2) a polarization beam splitter reflecting only one of said first light and said second light in said compound light.

32. The image reading system of claim 29, wherein said boundary substantially divides said angular aperture into two equal parts.

33. The image reading system of claim 32, wherein said selective reflection mirror comprises:
(b-1) a transparent substrate; and
(b-2) a selective photo-reflection film selectively formed on said transparent substrate;
and wherein said first region is an exposed surface of said selective photo-reflection film; and
said second region is an exposed surface of said transparent substrate.

34. The image reading system of claim 33, wherein said first light source means emits said first light in a direction perpendicular to said optical axis; and
said selective reflection mirror is inclined from said optical axis by 45°.

35. A method of reading respective images of a wiring pattern and a through hole of an printed board having first and second surfaces opposite to each other, in which said wiring pattern is formed on said first surface and said through hole is provided between said first and second surfaces, said method comprising the steps of:

(a) providing an imaging optical system;
(b) providing a selective reflection mirror covering only a part of an angular aperture of said imaging optical system, wherein said selective reflecting mirror is capable of reflecting a first light of a first optical character and capable of transmitting a second light of a second optical character;
(c) applying said first light from out of an angular aperture of said imaging optical system to said selective reflection mirror to direct said first light to said first surface of said printed board, thereby obtaining a reflected light through reflecting of said first light on said wiring pattern;
(d) applying said second light to said second surface of said printed board, thereby obtaining a transmitted light through transmittance of said second light through said through hole;
(e) obtaining a compound light consisting of said reflected light and said transmitted light;
(f) leading said compound light to said imaging optical system through a space in which said selective reflection mirror is located, wherein:
with respect to said reflected light included in said compound light, only a part thereof bypassing said selective reflection mirror is received by said selective reflection mirror; and
with respect to said transmitted light included in said compound light, both of a first thereof passing through said selective reflection mirror and a second part bypassing said selective reflection mirror are received by said selective reflection mirror;
(g) receiving with a light splitter said compound light having passed through said space to split said compound light into said reflected light and said transmitted light;
(h) receiving said reflected light with a first image sensor to obtain an image of said wiring pattern; and
(i) receiving said transmitted light with a second image sensor to obtain an image of said through hole.

36. The method of claim 35, wherein
said first light is a light having a first wavelength;
said second light is a light having a second wavelength; and said light splitter is a mirror reflecting only one of said first light and said second light in said compound light.

37. The method of claim 35, wherein
said first light is a light polarized in a first direction;
said second light is a light polarized in a second direction; and
said light splitter is a polarization beam splitter mirror reflecting only one of said first light and said second light in said compound light.

38. The method of claim 35, wherein
said selective reflection mirror has an edge located on an optical axis of said imaging optical system.

39. The method of claim 38, wherein
said selective reflection mirror comprises a transparent substrate and a selective photo-reflection film formed on said transparent substrate.

40. The method of claim 39, wherein said edge of said selective reflection mirror is processed into a wedge.

41. The method of claim 39, wherein
said edge of said selective reflection mirror is processed into a wedge.

42. An image reading system for reading respective images of a wiring pattern and a through hole of an printed board having first and second surfaces opposite to each other, in which said wiring pattern is formed on said first surface and said through hole is provided between said first and second surfaces, said image reading system comprising:
 (a) imaging optical system;
 (b) a selective reflection mirror covering only a part of an angular aperture of said imaging optical system and capable of reflecting a first light of a first optical characters and capable of transmitting a second light of a second optical character;
 (c) first light source means provided out of an angular aperture of said imaging optical system, for emitting said first light toward said selective reflection mirror to direct said first light to said first surface of said printed board and to obtain a reflected light through reflection of said first light on said wiring pattern;
 (d) second light source means provided in the said second surface side, for emitting said second light toward said second surface of said printed board to obtain a transmitted light through transmittance of said second light through said through hole;
wherein said reflected light and said transmitted light are overlapped with each other to form a compound light;
said compound light passes through a space in which said selective reflection mirror is provided and then enters said imaging optical system;
with respect to said reflected light includes in said compound light, only a part thereof bypassing said selective reflection mirror is received by said selective reflection mirror; and
with respect to said transmitted light included in said compound light, both of a first part thereof passing through said selective reflection mirror and a second part bypassing said selective reflection mirror are received by said selective reflection mirror;
 (e) light splitter means for receiving said compound light having passed through said imaging optical system to split said compound light into said reflected light and said transmitted light;
 (f) first image sensor means for receiving said reflected light with to obtain an image of said wiring pattern; and
 (g) second image sensor means for receiving said transmitted light to obtain an image of said through hole.

43. The image reading system of claim 42, wherein
said first light source means comprises:
(c-1) a first illuminator means for emitting light having a first wavelength as said first light:
said second light source means comprises;
(b-1) a second illuminator means for emitting light having a second wavelength as said second light; and
said light splitter means comprises:
(e-1) a mirror reflecting only one of said first light and said second light in said compound light.

44. The image reading system of claim 42, wherein
said first light source means comprises:
(c-2) a first illuminator means for emitting light polarized in a first direction as said first light;
said second light source means comprises:
(b-2) a second illuminator means for emitting light polarized in a second direction as said second light; and
said light splitter means comprises:
(e-2) a polarization light splitter reflecting only one of said first light and said second light in said compound light.

45. The image reading system of claim 42, wherein
said selective reflection mirror has an edge located on an optical axis of said imaging optical system.

46. The image reading system of claim 45, wherein
said edge substantially divides said angular aperture into two equal parts.

47. The image reading system of claim 45, wherein
said selective reflection mirror comprises a transparent substrate and a selective photo-reflection film formed on said transparent substrate.

* * * * *